United States Patent [19]
Koike et al.

[11] Patent Number: 5,445,888
[45] Date of Patent: Aug. 29, 1995

[54] HYDRAZINE COMPOUND, PROCESS FOR THE PREPARATION OF THE SAME, AND NONLINEAR OPTICAL ORGANIC MATERIAL

[75] Inventors: Tsuneaki Koike; Hideo Hama; Tooru Yamanaka, all of Sodegaura, Japan

[73] Assignee: Mitsui Petrochemical Industries, Ltd., Tokyo, Japan

[21] Appl. No.: 177,713

[22] Filed: Jan. 5, 1994

Related U.S. Application Data

[62] Division of Ser. No. 924,970, Aug. 5, 1992, abandoned.

[30] Foreign Application Priority Data

Aug. 6, 1991 [JP] Japan ..................... 3-196871

[51] Int. Cl.$^6$ .............................. B32B 9/04
[52] U.S. Cl. ..................... 428/411.1; 428/1; 428/333; 428/913; 564/149; 564/150; 564/151
[58] Field of Search .............. 564/149, 150, 151; 428/64, 67, 913, 212, 195, 411.1, 333, 1, 913

[56] References Cited

U.S. PATENT DOCUMENTS 2,706,732  4/1955  Duschinsky et al. .......... 564/151 X
2,706,733  4/1955  Duschinsky et al. .......... 549/314

FOREIGN PATENT DOCUMENTS 2018549  1/1990  Japan .

OTHER PUBLICATIONS

Chemical Abstract 94:102338 Hegarty et al. J. Chem. Soc. 1980.
Chemical Abstract 75:9793S Hegarty et al. J. Chem Soc. 1971.
CA 71(1969) 1014425.
CA 68 (1967) 593344.
CA 94 (1980) 9961n
CA Registry Handbook (1974).
CA 111 (1989) 1159846.
CA 113 (1990) 106287r.
CA 108 (1987) 131479j.
CA 106 (1986) 49627f.
CA 82 (1974) 111727e.
CA 77 (1972) 87420u.
CA 75 (1971) 62723v.
CA 75 (1969) 21093j.
Database WPIL Week 9102, Derwent Publications, Ltd. London, GB AN 91-012631 & JP-A-2 287 536 (Konica Corp.).
Database WPIL Week 9114, Derwent Publications, Ltd., London, GB; AN 91-097054 & JP-A-3 039 731 (Konica Corp.).
Chemical Abstracts, vol. 87, No. 17, 24 Oct. 1977, Columbus, Ohio, US.

(List continued on next page.)

*Primary Examiner*—Patrick J. Ryan
*Assistant Examiner*—William A. Krynski
*Attorney, Agent, or Firm*—Sherman and Shalloway

[57] ABSTRACT

A novel hydrazine compound represented by the formula (I) is disclosed.

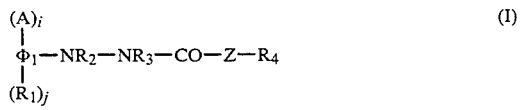

Also disclosed are a process for preparing the novel hydrazine compound comprising reacting a specific hydrazine compound and a specific acid halide, a nonlinear optical organic material comprising the hydrazine compound represented by the above formula (I), and a nonlinear optical organic element comprising the nonlinear optical organic material. The nonlinear optical organic material shows excellent nonlinear optical effect, and the material is favorably applied to nonlinear optical organic elements such as an optical wavelength conversion element and an electrooptical element.

36 Claims, 9 Drawing Sheets

OTHER PUBLICATIONS

Database WPIL Week 9009 Derwent Publications Ltd., London, GB; AN 90064254 & JP-A-2 018 549 (Konica Corp.).

Chemical Abstracts, vol. 110, No. 19, 8 May 1989, Columbus, Ohio.

Database WPIL Week 9122, Derwent Publications Ltd., London, GB; AN 91-159352 & JP-A-3 093 767 (Konica Corp.).

IEEE Journal of Quantum Electronics vol. 17, No. 9, 1981, New York, pp. 1593-1595 K Jain et al. 'New materials with large optical nonlinearities'.

Database WPIL Week 9143, Derwent Publications, Ltd., London, GB; AN 91-314117 & JP-A-3 209 225 (Dainippon Ink Chem. KK).

J. Chem. Soc., Perkin Transactions II, pp. 1381-1386 (1972).

HYDRAZINE COMPOUND, PROCESS FOR THE PREPARATION OF THE SAME, AND NONLINEAR OPTICAL ORGANIC MATERIAL

This application is a division of application Ser. No. 07/924,970, filed Aug. 5, 1992, now abandoned.

FIELD OF THE INVENTION

The present invention relates to a novel hydrazine compound, a process for preparing the novel hydrazine compound, a nonlinear optical organic material used in the field of optical information communication or optical information processing, and a nonlinear optical element comprising the nonlinear optical organic material, such as an optical wavelength conversion element or an electrooptical element.

BACKGROUND OF THE INVENTION

In the fields of optical information communication, optical information processing, etc., nonlinear optical organic materials have been recently paid attention. The nonlinear laser materials mean materials showing such nonlinear optical effects that they convert a light of a laser into a light having different wavelength and they are varied in the refractive index under application of electric voltage. Particularly, second-order nonlinear optical organic materials having such effect that they convert a light of a laser into a light having a wavelength of ½ of the laser wavelength (second harmonic generation) have been paid much attention as materials far superior to inorganic materials since the nonlinear optical organic materials were reported (ACS Symposium Series 233, 1983). For example, $KTiOPO_4$ (i.e., KTP) is known as the typical inorganic material, but development of a nonlinear optical organic material having higher nonlinear optical properties than KTP is expected.

The second-order nonlinear optical organic materials include those containing an aromatic ring, a donative substituent group and an accepting substituent group and having such a structure that $\pi$ electrons of the aromatic ring are polarized by the donative substituent group and the accepting substituent group in the molecule. The materials of this type is assumed to be extremely enhanced in the nonlinear optical response because nonlinear optical properties are produced on the $\pi$ electron sites.

However, para-nitroaniline which is expected to have high nonlinear optical response takes such a structure that the adjacent two molecules are inverted to each other when it is processed to be in the form of single crystal, this single crystal being essential for the nonlinear optical elements such as an optical wavelength conversion element and an electrooptical element in the practical use, resulting in losing of the nonlinear optical properties. That is, the nonlinear optical organic materials tend to lose the nonlinear optical properties when the adjacent molecules become to be centrally symmetric. For this reason, organic compounds have been synthesized in which a substituent group for getting rid of the symmetry of the adjacent molecules or a substituent group for imparting optical activity is introduced. For example, 2-methyl-4-nitroaniline synthesized as above has been confirmed to show high nonlinear optical properties.

The nonlinear optical organic materials tend to have higher nonlinear optical properties as the intramolecular polarizabilities thereof become higher, but when the intramolecular polarizabilities become too high, transference of electric charge occurs, and thereby the materials lose transparency. Further, the wavelength of the second harmonic generation and the maximum absorption wavelength $\lambda_{max}$ of the nonlinear optical organic material are coincident with each other, so that the second harmonic generation cannot be efficiently taken out.

For obtaining nonlinear optical organic materials, there have been proposed compounds in which a nitro group having high acceptability and an amino group having high donative properties are incorporated at the both ends of a linear molecule such as stilbene. However, these compounds have such problems that the adjacent molecules are apt to be centrally symmetric and the transparency is not so high.

In order to solve those problems, various methods such as a method of limiting the length of the $\pi$ electron conjugation system in the molecule and a method of incorporating a hetero atom into the aromatic ring have been tried, but any absolute solution to the problems has not been found out yet.

Further, there is other problem that any nonlinear optical organic material in a form of single crystal having suitable size for using as the nonlinear optical element cannot been obtained by the conventional processes. That is, almost all of the conventional nonlinear optical organic materials are extremely small sized needle crystals or single crystals having less than 1 $mm^3$, and a nonlinear optical organic material of single crystal having 1 $mm^3$, especially more than 5 $mm^3$ has been hardly obtained conventionally.

OBJECT OF THE INVENTION

The present invention is made in the light of such circumstances as mentioned above, and the object of the invention is to provide a novel hydrazine compound employable for the above-mentioned nonlinear optical materials, a process for preparing the novel hydrazine compound, and a novel nonlinear optical organic material in which the adjacent molecules are hardly made centrally symmetric and which shows high transparency and excellent nonlinear optical properties, particularly a nonlinear optical organic material of single crystal having more than 1 $mm^3$ when the material is a single crystal. Further, the object of the invention is to provide a nonlinear optical element comprising the novel nonlinear optical organic material, such as a wavelength conversion element or an electrooptical element, and an optical modulation device provided with the nonlinear optical element.

SUMMARY OF THE INVENTION

The novel hydrazine compound of the present invention is a hydrazine compound represented by the following formula (I):

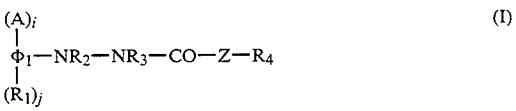

wherein A is an accepting substituent group; $\Phi_1$ is an aromatic ring or a heterocyclic ring; $R_1$ to $R_3$ are each independently a hydrogen atom or a group selected from the group consisting of an alkyl group, an aryl group, an aralkyl group and an alkyloxy group; $R_4$ is a hydrogen atom or a group selected from the group consisting of an alkyl group, an alkenyl group and a phenyl group; when $R_4$ is an alkyl group or an alkenyl group, the alkyl group or the alkenyl group may have an hydroxyl group and/or a halogen atom, and a divalent hetero atom or a divalent group containing a hetero atom may be present between adjacent two carbon atoms of the alkyl group or the alkenyl group; B is a direct bond or an oxygen atom; and each of i and j is an integer of 1 or more.

The hydrazine compound represented by the above formula (I) is prepared by a process comprising a step of causing a hydrazine compound represented by the following formula (III) to react with an acid halide represented by the following formula (IV):

wherein A, $\Phi_1$, $R_1$ to $R_3$, i and j have the same meanings as defined above;

wherein $R_4$ and Z have the same meanings as defined above, and X is a halogen atom.

The nonlinear optical organic material of the invention comprises the hydrazine compound represented by the above formula (I).

The nonlinear optical element of the invention is an element comprising the above-mentioned nonlinear optical organic material.

Figure 1:
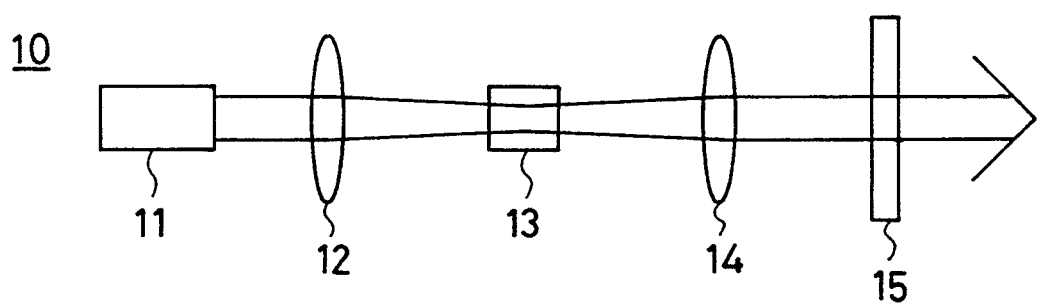
FIG. 1 is a view illustrating an example of an optical modulation device according to the invention.

Illustration of numerical symbols
10, 20: second harmonic generation device
30: optical modulation device
11, 21, 31: laser beam source
12, 14, 22, 32: condenser lens
13: nonlinear optical element
15: infrared rays cut-off filter
23: core material
24: cladding material
33: wave-guiding path
34: substrate
35: electrode

DETAILED DESCRIPTION OF THE INVENTION

The novel hydrazine compound of the invention, the process for preparing the novel hydrazine compound and the nonlinear optical organic material of the invention are described in detail hereinafter.

The novel hydrazine compound of the invention is represented by the above-mentioned formula (I).

Concrete examples of the hydrazine compound are the following compounds (1) to (26).

Compound (1):

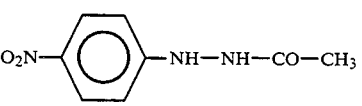

Compound (2):

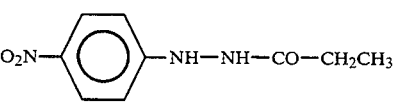

Compound (3):

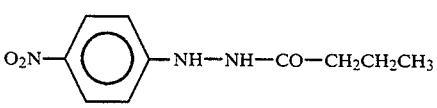

Compound (4):

-continued

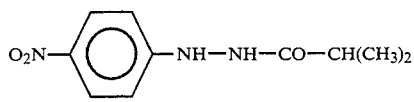

Compound (5):

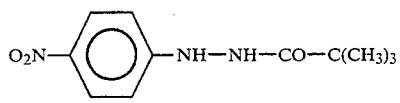

Compound (6):

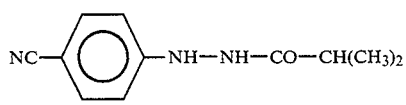

Compound (7):

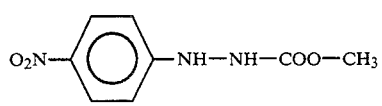

Compound (8):

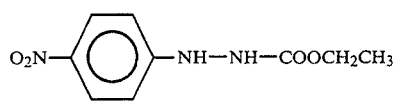

Compound (9):

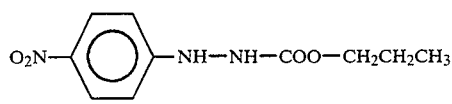

Compound (10):

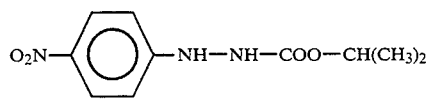

Compound (11):

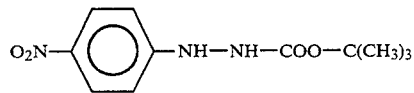

Compound (12):

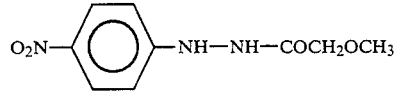

Compound (13):

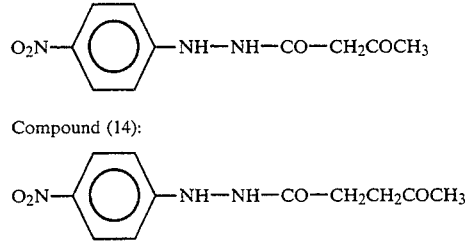

Compound (14):

Compound (15):

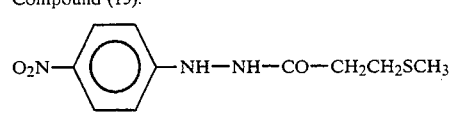

Compound (16):

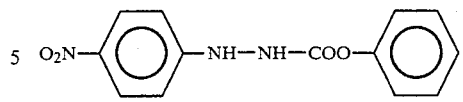

Compound (17):

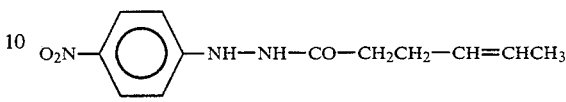

Compound (18):

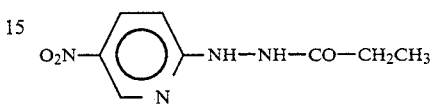

Compound (19):

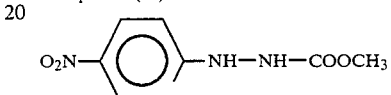

Compound (20):

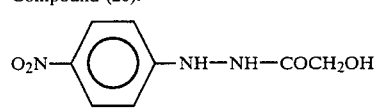

Compound (21):

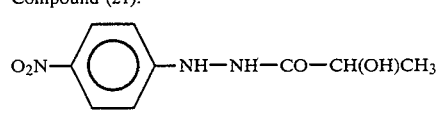

Compound (22):

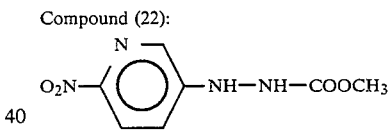

Compound (23):

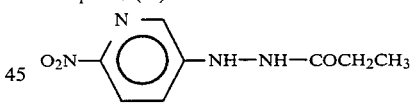

Compound (24):

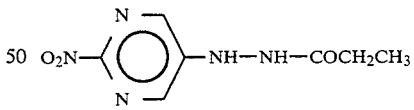

Compound (25):

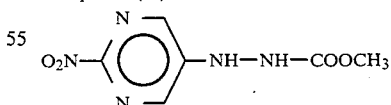

Compound (26):

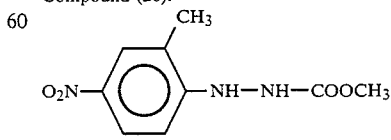

The novel hydrazine compound represented by the above formula (I) is prepared by conducting a condensation reaction of a hydrazine compound having the above formula (III) and an acid halide represented by the above formula (IV) (preferably acid chloride), preferably in the presence of a base.

Examples of the base employable for the reaction include pyridine, trimethylamine and triethylamine. Of these, particularly preferred is pyridine or trimethylamine. These bases may be used in combination.

The reaction to produce the above-mentioned hydrazine compound presented by the formula (I) is illustrated below using a hydrazine compound represented by the following formula (V) and acid chloride represented by the following formula (VI) as starting materials:

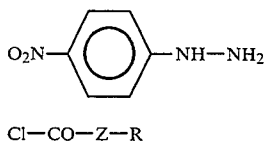

(V)

Cl—CO—Z—R (VI)

wherein Z is a direct bond or an oxygen atom, and R is an alkyl group of 1-4 carbon atoms.

In this case, the hydrazine compound represented by the formula (I) is synthesized by the reaction of the following formula.

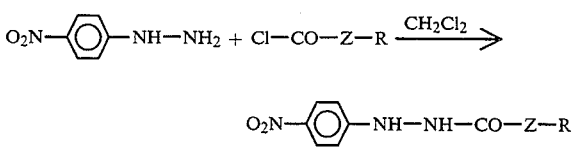

As is clear from the reaction formula, HCl is produced in the condensation of the hydrazine compound and the acid cloride, and it is necessary to neutralize HCl to advance the reaction. For neutralization of HCl, a base is generally used in an amount of 1.0 to 5 mol, preferably 2 to 5 mol, per 1 mol of the hydrazine derivative or the acid chloride.

The reaction is carried out generally in a liquid phase. In this reaction, a solvent which is chemically inert to the hydrazine derivative and acid chloride used as the starting materials and also inert to the resulting carbohydrazide derivative and capable of dissolving the hydrazine derivative and the acid chloride is used. Examples of the solvents include various solvents such as aromatic hydrocarbon solvents, aliphatic saturated hydrocarbon solvents, aliphatic saturated halogenated hydrocarbon solvents, aliphatic unsaturated hydrocarbon solvents and ether solvents. Particularly preferred are dichloromethane and THF. These solvents can be used singly or in a mixture of two or more kinds.

The above-mentioned reaction is carried out at a temperature generally in the range of −20° to 100° C., preferably in the range of 0° to 100° C. Further, the reaction can be carried out at a pressure in the range of a reduced pressure to 60 kg/cm², but it is preferably carried out at a pressure of 0 to 30 kg/cm², more preferably 0 to 5 kg/cm². The reaction time is appropriately determined in accordance with the reaction temperature, the reaction pressure, etc, and is not specifically limited, but the reaction time is generally in the range of 5 to 100 hours, preferably 1 to 10 hours.

The reaction is normally conducted in an inert atmosphere such as an argon atmosphere or a nitrogen atmosphere.

The hydrazine compound represented by the formula (I) according to the invention can be also obtained by a dehydration reaction of a hydrazine compound and a carboxylic acid. In this dehydration reaction, a dehydrating agent such as DCC (N,N'-dicyclohexylcarbodiimide) is employed.

The nonlinear optical organic material according to the invention comprises the hydrazine compound represented by the above formula (I). By linking the accepting substituent group A to $\Phi_1$, polarization of $\Phi_1$ is produced thereby to accelerate polarization of the whole compound represented by the formula (I).

The accepting substituent group A preferably has Hammet value $\sigma$ satisfying the condition of $0 < \sigma < 0.8$. Examples of such substituent groups include nitro group, cyano group, trifluoromethyl group, trifluoromethoxy group, trifluoromethylthio group, carbamoyl group, nitroso group, cyanato group, thiocyanato group, isocyanato group, formyl group, alkoxycarbonyl group (e.g., methoxylcarbonyl and ethoxycarbonyl), halogenated alkoxycarbonyl group, acetyl group, propinoyl group, halogenated acyl group, sulfo group, sulfino group, sulfeno group and halogen atom. Of these, preferred is nitro group or cyano group.

One or plural accepting substituent groups A are linked to $\Phi_1$, and when plural accepting substituent groups A are linked to $\Phi_1$, they may be the same or different from each other.

The accepting substituent group(s) A is linked to $\Phi_1$ in such a manner that the polarization of $\Phi_1$ would be accelerated. For example, when $\Phi_1$ is a benzene ring, the accepting substituent group A is linked to $\Phi_1$ preferably at the para-position to the —NR$_2$NR$_3$CO— group. Otherwise, when a plurality of accepting substituent groups A are present, they are linked to $\Phi_1$ preferably at the para-position and the meta-position to the —NR$_2$NR$_3$CO— group.

$\Phi_1$ in the above formula (I) is an aromatic ring or a heterocyclic ring. Among the aromatic rings, preferred is a benzene ring. Among the heterocyclic rings, preferred is a 5-membered or 6-membered heterocyclic ring, and particularly preferred is a 5-membered heterocyclic ring. Those aromatic rings or the heterocyclic rings serve to form a field of electron resonance, and owing to those rings nonlinear optical effect is effectively shown. Concrete examples of the aromatic rings or the heterocyclic rings used as $\Phi_1$ are as follows.

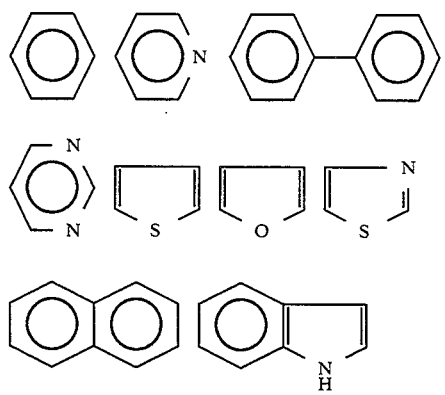

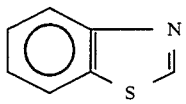

R₁ to R₃ in the above formula (I) are each independently a hydrogen atom or a group selected from the group consisting of an alkyl group, an aryl group, an aralkyl group and an alkyloxy group. Among them, a hydrogen atom or an alkyl group, particularly a methyl group or an ethyl group, is preferred as $R_1$, and a hydrogen atom is preferred as each of $R_2$ and $R_3$. $R_1$ may be linked to not only a carbon atom of the aromatic ring or the heterocyclic ring but also a hereto atom of the heterocyclic ring, such as a N atom.

The above-mentioned alkyl group may be of a straight-chain form or a branched-chain form, and has 1-6 carbon atoms, preferably 1-3 carbon atoms. Examples of such alkyl groups include straight-chain alkyl groups such as methyl group, ethyl group, n-propyl group and n-butyl group; second-order alkyl groups such as isopropyl group, sec-butyl group and sec-amyl group; and tertiary alkyl groups such as tert-butyl group and tert-amyl group.

The above-mentioned aryl group may have a substituent group. Concrete examples of such aryl groups include phenyl group, naphthyl group, tolyl group and xylyl group.

Concrete examples of the above-mentioned aralykyl groups include benzyl group, phenetyl group, α-methylbenzyl group and tolylmethyl group.

The above-mentioned alkyloxy group may be of a straight-chain form or a branched-chain form, and has 1-6 carbon atoms, preferably 1-3 carbon atoms. Concrete examples of such alkyloxy groups include straight-chain alkyloxy groups such as methoxy group, ethoxy group, n-propoxy group and n-butoxy group; second-order alkyloxy groups such as isopropoxy group, sec-butoxy group and secamyloxy group; and tertiary alkyloxy groups such as tert-butoxy group and tert-amyloxy group.

In the compounds as mentioned above, $R_1$ is preferably configured at the position so that the adjacent molecules are not made centrally symmetric. For example, when $\Phi_1$ is a benzene ring, $R_1$ is preferably linked to $\Phi_1$ at the ortho-position to the —NR₂NR₃CO— group. In this case, two of $R_1$ may be each linked to $\Phi_1$ at the ortho-position to the —NR₂NR₃CO— group. When a plurality of $R_1$ are linked to $\Phi_1$, they may be the same as or different from each other.

$R_2$ and/or $R_3$ is preferably an optically active group. If $R_2$ and/or $R_3$ is an optically active group, symmetry of the molecules is broken. Therefore, when a single crystal is formed, the adjacent molecules hardly become centrally symmetric, and the nonlinearity can be effectively retained. The optically active group used herein means a group having an asymmetric carbon atom, for example, a substituent group in which three different groups (methyl group, ethyl group and hydrogen atom) are linked to one carbon atom.

$R_4$ in the above formula (I) is a hydrogen atom or a group selected from the group consisting of an alkyl group, an alkenyl group and a phenyl group. Each of the alkyl group and the alkenyl group may be of a straight-chain form or a branched-chain form, and may have a hydroxyl group and/or a halogen atom. Further, between the adjacent two carbon atoms in the alkyl group or the alkenyl group may be present a divalent hetero atom (e.g., O, S and Se) or a divalent group containing the divalent hetero atom or a hetero atom (e.g., N, Z, Si and Ge).

Examples of the divalent groups are given below.

—CO— group,
—NH— group,
—N(CH₃)— group,
—ZH— group,
—Z(CH₃)— group,
—SiH₂— group,
—Si(CH₃)₂— group,

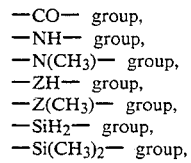

—Si(OCH₃)₂— group,

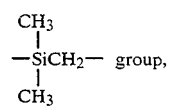

—GeH₂— group,
—Ge(CH₃)₂— group, and

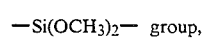

Z in the above formula (I) is a direct bond or an oxygen atom. When —ZR₄ is an alkyl group, this alkyl group is preferably an ethyl group or a n-propyl group. When —ZR₄ is an alkoxy group, this alkoxy group is preferably a methoxy group.

In the case of using the hydrazine compound represented by the formula (I) as a nonlinear optical organic material, the hydrazine compound preferably has at least one heavy hydrogen.

The nonlinear optical organic material according to the invention is composed of a compound represented by the above formula (I), and used in the crystallized form for producing a nonlinear optical element. Generally, the compound represented by the formula (I) is used singly for the nonlinear optical organic material of the invention, but a plurality of the compounds represented by the formula (I) may be used therefor.

The crystal of the compound represented by the formula (I) may be a co-crystal of the compound and other component having a similar crystalline structure to that of the compound, or it may be a polycrystal, but preferably it is a single crystal.

Further, the nonlinear optical organic material according to the invention is a composite composed of the compound represented by the above formula (I) and a transparent polymer binder.

The single crystal as mentioned above can be obtained, for example, by dissolving the compound represented by the formula (I) in an appropriate solvent such as dimethylformamide or ethanol and then vaporizing the solvent, or lowering the temperature of the resulting solution to crystallize the compound contained in the solution. Otherwise, the single crystal can be also obtained by heating and melting the compound of the formula (I) and then cooling the molten compound to crystallize the compound, or by vapor phase growing the compound of the formula (I) by means of vacuum deposition, molecular beam epitaxial method or the like.

By the use of the nonlinear optical organic material of the invention, a large sized single crystal of rectangular parallelepiped having not less than 1 mm$^3$ can be obtained by the above-mentioned processes, and especially by the use of methyl-3-(p-nitrophenyl)carbazate (aforementioned compound (7)) in the compounds represented by the formula (I), a large sized single crystal of having not less than 5 mm$^3$ can be easily obtained.

The large sized single crystal made of the nonlinear optical organic material of the invention is subjected to a cutting procedure and a processing procedure to prepare a nonlinear optical element of the invention.

In the case of forming the nonlinear optical element of the invention from the thin film single crystal obtained as above, the thickness of the thin film single crystal is desired to be not less than 1 μm.

The composite composed of the compound of one or more kinds represented by the above formula (I) and a transparent polymer can be obtained, for example, by a process comprising the steps of dispersing the compound of at least one kind represented by the formula (I) in a polymer matrix, then applying an electric voltage to the resulting dispersion, with heating of the dispersion at a temperature of not lower than the glass transition point, to orientate the above-mentioned compound contained in the dispersion, and cooling and solidifying the dispersion with keeping the orientation.

The nonlinear optical element according to the invention can be obtained by processing the above-obtained composite composed of the compound of at least one kind represented by the formula (I) and the transparent polymer into a desired shape.

The optical modulation device according to the invention is provided with the above-described nonlinear optical element of the invention, and is employed as a second harmonic generation device, an optical switch, etc.

FIG. 1 shows one example of the second harmonic generation device according to the invention. In FIG. 1, the second harmonic generation device 10 includes a laser beam source 11, a condensing lens 12, a nonlinear optical element 13, a condensing lens 14 and an infrared rays cut-off filter 15.

In the second harmonic generation device 10, a laser beam released from the laser beam source 11 is converged on the nonlinear optical element 13 by the condensing lens 12. When the laser beam is incident on the nonlinear optical element 13, a light having a wavelength of ½ of the laser wavelength is generated by the nonlinear optical element, and the light containing a basic wave of the laser beam and the second-order harmonic wave is released from the nonlinear optical element 13. This light is converted into an approximately parallel light by the condensing lens 14. By passing of the approximately parallel light through the infrared rays cut-off filter 15, a light having the second harmonic is selectively output.

Figure 2:
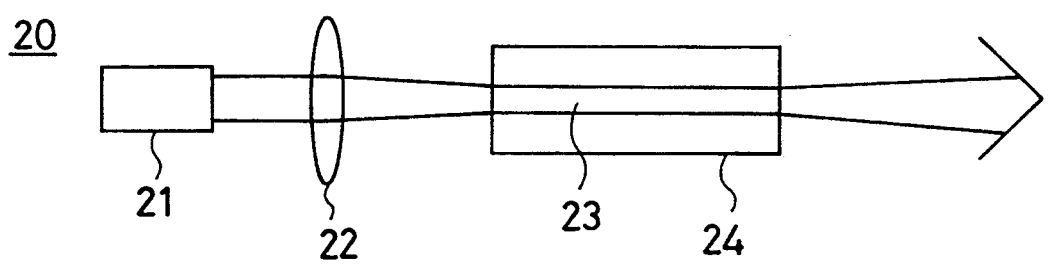
FIG. 2 is a view illustrating another example of an optical modulation device according to the invention.

A second harmonic generation device 20 shown in FIG. 2 includes a laser beam source 21, a condensing lens 22, a core material 23 made of the nonlinear optical organic element according to the invention, and a cladding material 24 made of a transparent substance having a refraction index different from that of the core material 23, such as a glass. The core material 23 is covered with the cladding material 24.

In the second harmonic generation device 20, a laser beam released from the laser beam source 21 is incident on one end of the core material 23 by way of the condensing lens 22. The laser beam entered from one end of the core material 23 is transmitted within the core material 23. During the transmission of the laser beam within the core material 23, a second harmonic generation occurred, and a light having the wavelength of ½ of the input laser wavelength is output from the other end of the core material 23.

Figure 3:
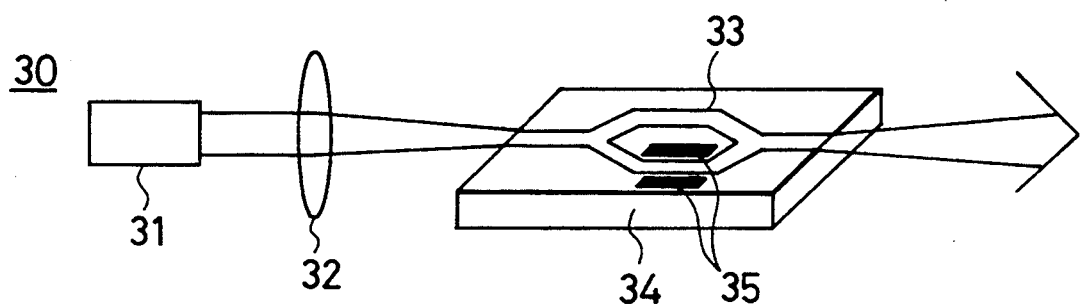
FIG. 3 is a view illustrating another example of an optical modulation device according to the invention.

An optical modulation device 30 shown in FIG. 3 includes a laser beam source 31, a condensing lens 32 and a substrate 34 provided with a wave-guiding path 33 made of the nonlinear optical organic element according to the invention. The wave-guiding path 33 is branched on the substrate 34 to form two branched paths having the same optical path length as each other, and these two paths get together again. On the both sides of one of the branched paths are arranged a pair of electrodes 35 connected to an external electric source (not shown).

In the optical modulation device 30, a laser beam released from the laser beam source 31 is incident on one end of the wave-guiding path 33 by way of the condensing lens 32 and is branched along the above-mentioned branched paths. Then, the laser beams on the branched paths get together and output from the other end of the wave-guiding path 33. When an electric voltage is applied to a pair of the electrodes 35, the refraction index of the nonlinear optical organic material which forms the branched path sandwiched between a pair of the electrodes 35 varies, and thereby the phase of the laser beam passing through the branched path is modulated. As a result, the phase and the intensity of the output light which is a synthetic light of the laser beams passing through both of the branched paths can be changed. This optical modulation device can be utilized as an optical switch, etc.

EFFECT OF THE INVENTION

As described above, the nonlinear optical organic material according to the invention is composed of the compound represented by the above formula (I). In the optical material, a field of resonance is given by the $\Phi_1$ ring, and the molecular polarization and the molecular configuration are controlled with good balance owing to A and $R_1$ to $R_4$. Moreover, the adjacent molecules are not made centrally symmetric, so that the nonlinear organic optical material shows excellent nonlinear optical effect.

Accordingly, the nonlinear optical organic material of the invention can be favorably applied to nonlinear optical elements such as an optical wavelength conversion element and an electrooptical element utilizing the second-order nonlinear optical effect.

EXAMPLE

The present invention is further described by the following examples, but the examples are given by no means to restrict the invention.

EXAMPLE 1

Into a 300 ml three-necked flask were introduced 50 ml of dichloromethane and 1.54 g of p-nitrophenylhydrazine. To the mixture in the flask was added 5 cc of pyridine under stirring of the mixture at room temperature, and then 1.5 cc of propionyl chloride having been beforehand dissolved in dichloromethane was slowly dropped into the resulting mixture through a dropping funnel, to immediately give an yellow precipitate.

The reaction liquid was further stirred at room temperature for 12 hours, and then completion of the reaction was confirmed by means of thin-layer chromatography. Thereafter, the excess propionyl chloride in the reaction liquid was hydrolyzed, and an aqueous solution of $NaHCO_3$ was added to the reaction liquid to separate the reaction liquid into an aqueous phase and an oily phase containing a large amount of the reaction product.

To the obtained aqueous phase was added dichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was precipitated again using acetone, to obtain 1.30 g of a purified product.

The purified product obtained as above had a melting point of 209° to 210° C. when measured in accordance with a DSC method.

Figure 4:
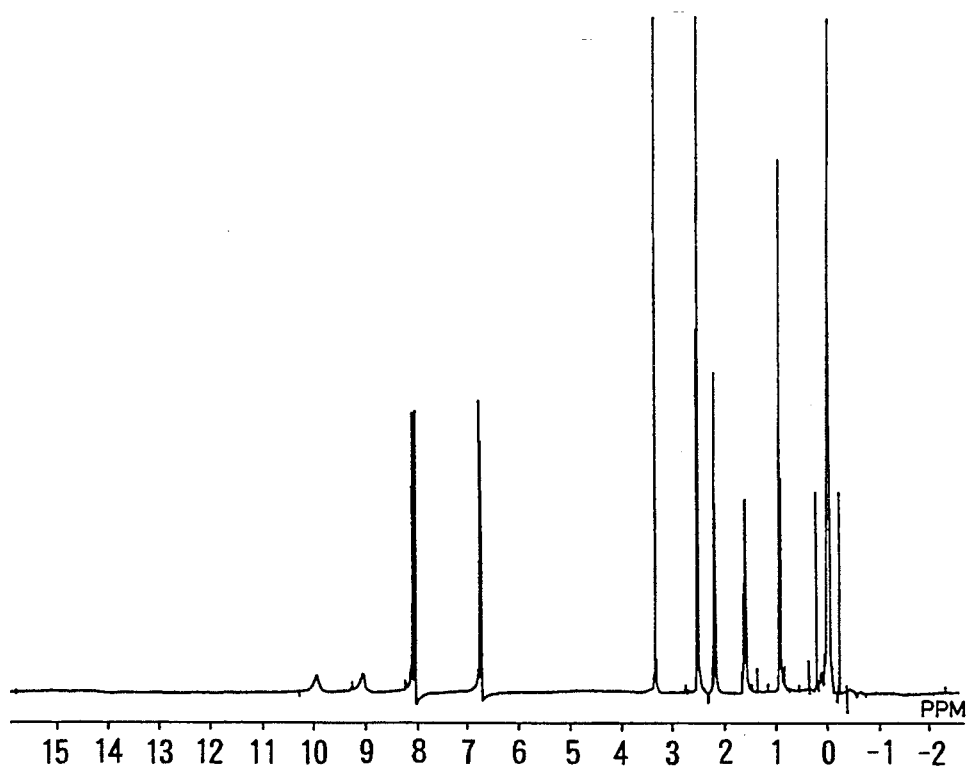
FIG. 4 is a $^1$H nucleus magnetic resonance spectrum chart of 4'-nitrophenyl-ethylcarbohydrazide, a novel hydrazine compound of the invention.

Further, the purified product was dissolved in DMSO (dimethyl sulfoxide). Using the resulting solution, a $^1H$ nucleus magnetic resonance spectrum of the purified product was measured. A chart of the obtained $^1H$ nucleus magnetic resonance spectrum is shown in FIG. 4.

The results obtained by analysis of peaks of this chart are as follows.

$^1H$ nucleus magnetic resonance ($\delta$ p.p.m.)
1.09 (t, 3H, $8H_z$, —$CH_3$)
2.24 (q, 2H, $7H_z$, —$CH_2$—)
6.75 (d, 2H, $9H_z$, ring proton)
8.07 (d, 2H, $9H_z$, ring proton)
9.02 (s, 1H, —NH—)
9.93 (s, 1H, —NH—)

Figure 5:
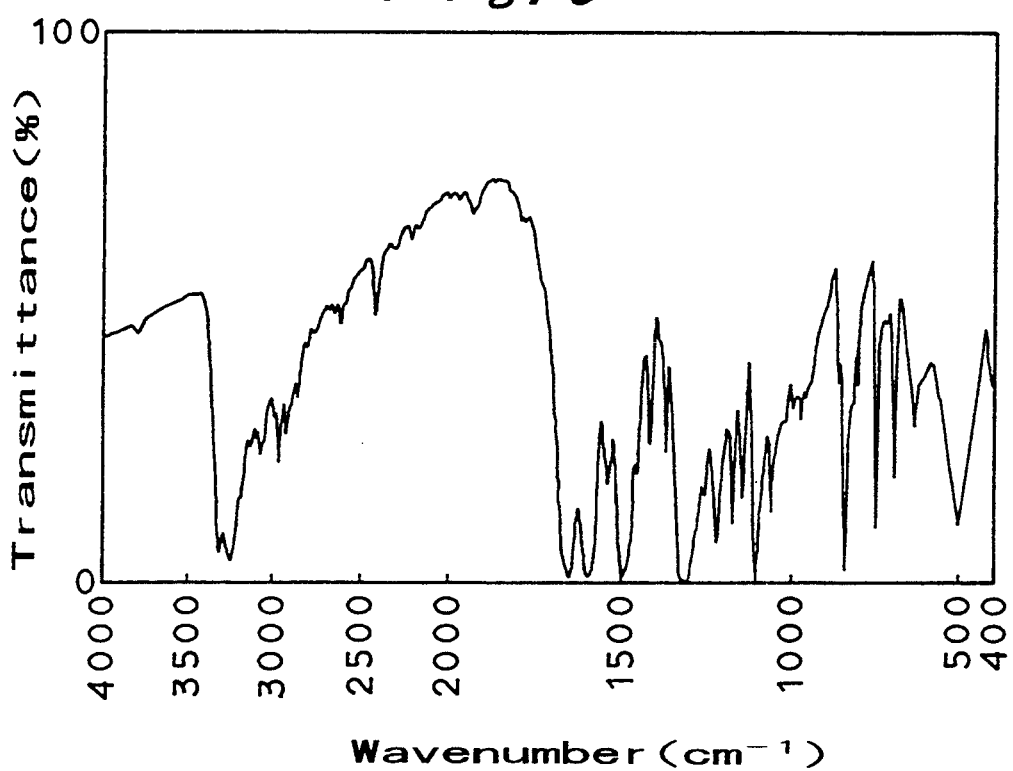
FIG. 5 is an infrared absorption spectrum chart of 4'-nitrophenyl-ethylcarbohydrazide, a novel hydrazine compound of the invention.

Furthermore, an infrared absorption spectrum of the purified product was measured. A chart of the obtained infrared absorption spectrum is shown in FIG. 5.

From the results obtained in the above, the purified product was identified to be 4'-nitrophenylethylcarbohydrazide (aforementioned compound (2)).

Subsequently, a powder of the aforementioned compound (2) was measured on the SHG intensity by a powder method. In this measurement, an YAG laser was employed. The SHG intensity of the powder was 24 times of the SHG intensity of an urea powder measured in the same manner as above.

Further, a powder of the aforementioned compound (2) was dissolved in a solvent of dimethylformamide (DMF), and the resulting solution was allowed to stand for about 10 days at room temperature. As a result, a single crystal having a size of $8 \times 5 \times 2$ $mm^3$ was obtained. The size of the single crystal corresponded to about 5 times of the 5 size of a single crystal obtained by growing 2-methylnitroaniline (MNA) in the similar manner.

Furthermore, when the single crystal of the compound (2) was irradiated with an YAG laser (continuous wave, wavelength: 1,064 nm, output: 175 mW), a keen peak of a SH light (532 nm) corresponding to the phase matching was obtained only in the case of a specific incident angle. Then, the intensity of the SH light was measured. As a result, the obtained intensity was a large value which was 3 times of an intensity obtained in the case of using a KTP crystal (sample length: 5 mm).

EXAMPLE 2

Into a 300 ml three-necked flask were introduced 70 ml of dichloromethane and 0.8 g of p-nitrophenylhydrazine. To the mixture in the flask was added 3 cc of pyridine under stirring of the mixture at room temperature, and then 0.8 cc of n-butyl chloride having been beforehand dissolved in dichloromethane was slowly dropped into the resulting mixture through a dropping funnel, to immediately give an yellow precipitate.

The reaction liquid was further stirred at room temperature for 12 hours, and then completion of the reaction was confirmed by means of thin-layer chromatography. Thereafter, the excess n-butyl chloride in the reaction liquid was hydrolyzed, and an aqueous solution of $NaHCO_3$ was added to the reaction liquid to separate the reaction liquid into an aqueous phase and an oily phase containing a large amount of the reaction product.

To the obtained aqueous phase was added dichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was developed by means of column chromatography using acetone/dichloromethane (¼ volume ratio) as a developing solution. The main component obtained by column chromatography was precipitated again using acetone, to obtain 1.35 g of a purified product.

The purified product obtained as above had a melting point of 177° to 178° C. when measured in accordance with a DSC method.

Further, a mass spectrum of the purified product was measured. As a result, m/Z of the purified product was 223 (100).

Figure 6:
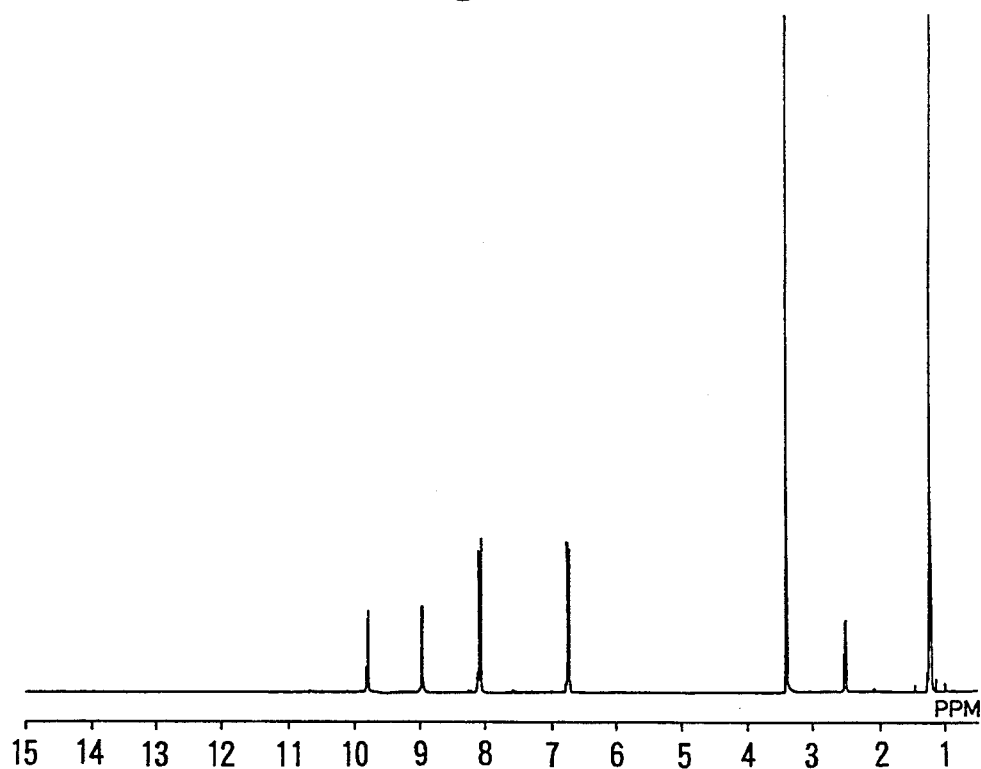
FIG. 6 is a $^1$H nucleus magnetic resonance spectrum chart of 4'-nitrophenyl-n-propylcarbohydrazide, a novel hydrazine compound of the invention.

Furthermore, the purified product was dissolved in DMSO (dimethyl sulfoxide). Using the resulting solution, a $^1H$ nucleus magnetic resonance spectrum of the purified product was measured. A chart of the obtained $^1H$ nucleus magnetic resonance spectrum is shown in FIG. 6.

The results obtained by analysis of peaks of this chart are as follows.

$^1H$ nucleus magnetic resonance ($\delta$ p.p.m.)
0.90 (t, 3H, $8H_z$, —$CH_3$)
1.57 (q, 2H, $7H_z$, —$CH_2$—)
2.18 (t, 2H, $8H_z$, —$CH_3$)
6.75 (d, 2H, $9H_z$, ring proton)
8.07 (d, 2H, $9H_z$, ring proton)
9.06 (s, 1H, —NH—)
9.93 (s, 1H, —NH—)

Figure 7:
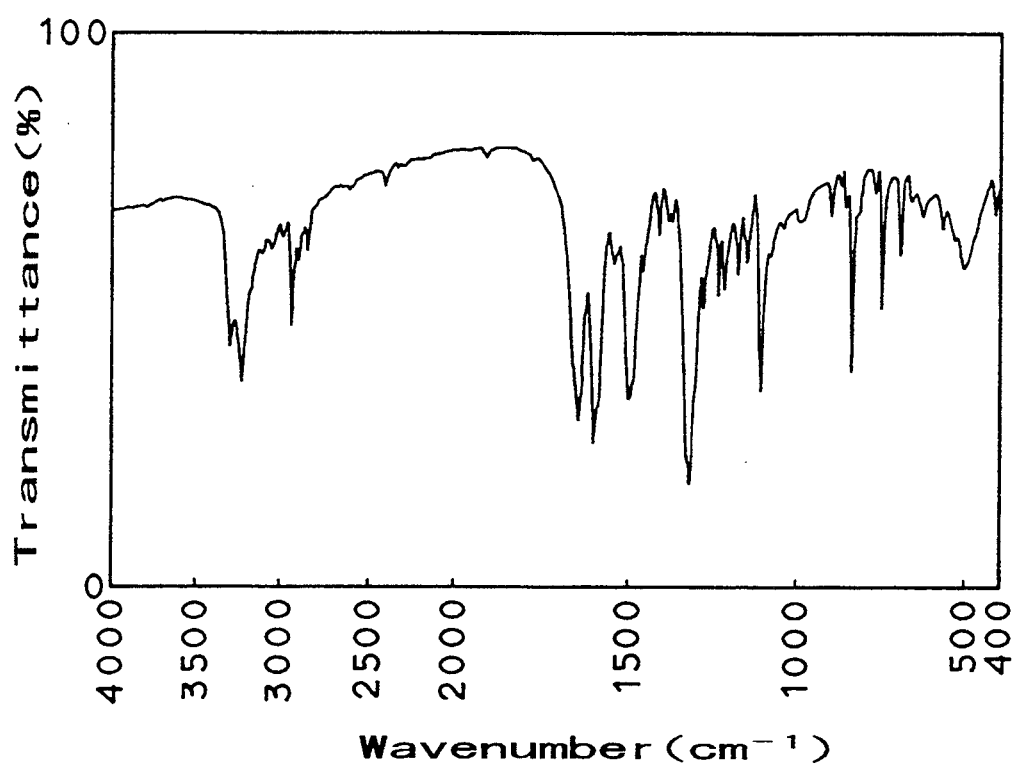
FIG. 7 is an infrared absorption spectrum chart of 4'-nitrophenyl-n-propylcarbohydrazide, a novel hydrazine compound of the invention.

Further, an infrared absorption spectrum of the purified product was measured. A chart of the obtained infrared absorption spectrum is shown in FIG. 7.

From the results obtained in the above, the purified product was identified to be 4'-nitrophenyl-n-propylcarbohydrazide (aforementioned compound (3)).

A powder of the obtained compound (3) was measured on the SHG intensity in the same manner as described in Example 1. As a result, the SHG intensity of this powder was 12.1 times of the SHG intensity of an urea powder measured in the same manner as above.

Then, a single crystal of the aforementioned compound (3) was prepared in the same manner as described in Example 1. The obtained single crystal had a size of 10×6×4 mm³. Further, the single crystal of the compound (3) obtained as above was subjected to an X-ray structural analysis. As a result, the spatial group belonged to orthorhombic system (P2₁2₁2₁), and the lattice constants were as follows.

a = 12.43 angstroms
b = 19.46 angstroms
c = 4.67 angstroms

Furthermore, using the obtained single crystal, the intensity of the SH light was measured in the same manner as described in Example 1. As a result, the obtained intensity was a large value which was 3.5 times of an intensity obtained in the case of using a KTP crystal (sample length: 5 mm).

EXAMPLE 3

Into a 300 ml three-necked flask were introduced 50 ml of dichloromethane and 0.77 g of p-nitrophenylhydrazine. To the mixture in the flask was added 2.5 cc of pyridine under stirring of the mixture at room temperature, and then 0.9 cc of trimethylacetyl chloride having been beforehand dissolved in dichloromethane was slowly dropped into the resulting mixture through a dropping funnel, to immediately give an yellow precipitate.

The reaction liquid was further stirred at room temperature for 12 hours, and then completion of the reaction was confirmed by means of thin-layer chromatography. Thereafter, the excess trimethylacetyl chloride in the reaction liquid was hydrolyzed, and an aqueous solution of NaHCO₃ was added to the reaction liquid to separate the reaction liquid into an aqueous phase and an oily phase containing a large amount of the reaction product.

To the obtained aqueous phase was added dichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was developed by means of column chromatography using acetone/dichloromethane (¼ volume ratio) as a developing solution. The main component obtained by column chromatography was precipitated again using acetone, to obtain 0.426 g of a purified product.

The purified product obtained as above had a melting point of 166° to 167° C. when measured in accordance with a DSC method.

Figure 8:
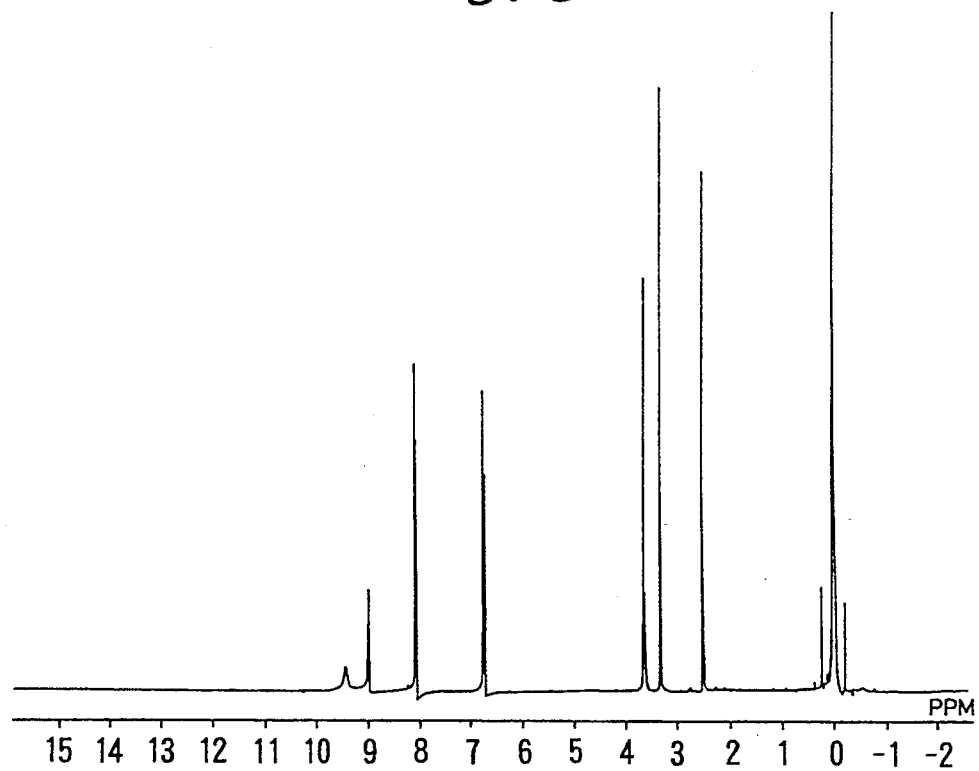
FIG. 8 is a $^1$H nucleus magnetic resonance spectrum chart of 4'-nitrophenyl-t-butylcarbohydrazide, a novel hydrazine compound of the invention.

Further, the purified product was dissolved in DMSO (dimethyl sulfoxide). Using the resulting solution, a ¹H nucleus magnetic resonance spectrum of the purified product was measured. A chart of the obtained ¹H nucleus magnetic resonance spectrum is shown in FIG. 8.

The results obtained by analysis of peaks of this chart are as follows.

¹H nucleus magnetic resonance (δ p.p.m.)
1.21 (s, 9H, —(CH₃)₃)
6.71 (d, 2H, 9H$_z$, ring proton)
8.08 (d, 2H, 9H$_z$, ring proton)
8.96 (s, 1H, —NH—)
9.79 (s, 1H, —NH—)

Figure 9:
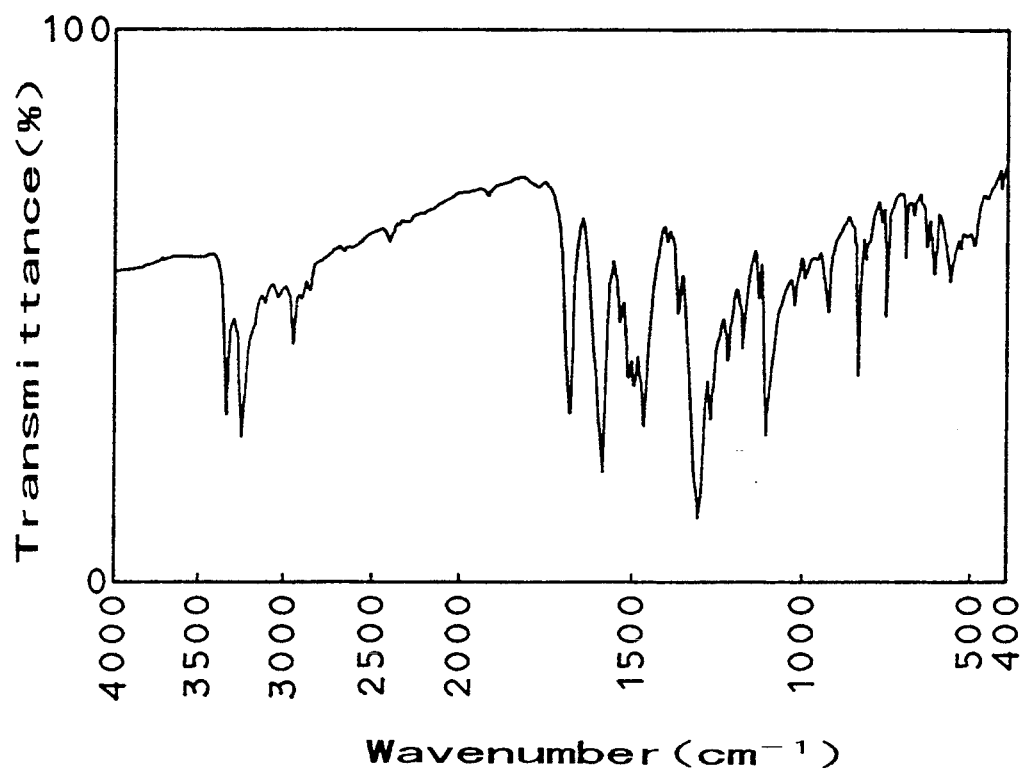
FIG. 9 is an infrared absorption spectrum chart of 4'-nitrophenyl-t-butylcarbohydrazide, a novel hydrazine compound of the invention.

Furthermore, an infrared absorption spectrum of the purified product was measured. A chart of the obtained infrared absorption spectrum is shown in FIG. 9.

From the results obtained in the above, the purified product was identified to be 4'-nitrophenyl-t-butylcarbohydrazide (aforementioned compound (5)).

A powder of the obtained compound (5) was measured on the SHG intensity in the same manner as described in Example 1. As a result, the SHG intensity of this powder was 1.0 time of the SHG intensity of an urea powder measured in the same manner as above.

Then, a single crystal of the aforementioned compound (5) was prepared in the same manner as described in Example 1. The obtained single crystal had a size of 5×3×1 mm³. Further, using the obtained single crystal, the intensity of the SH light was measured in the same manner as described in Example 1. As a result, the obtained intensity was a value which was 0.5 time of an intensity obtained in the case of using a KTP crystal (sample length: 5 mm).

EXAMPLE 4

Into a 300 ml three-necked flask were introduced 100 ml of dichloromethane and 0.77 g of p-nitrophenylhydrazine. To the mixture in the flask was added 2.50 cc of pyridine under stirring of the mixture at room temperature, and then 0.8 cc of methyl chloroformate having been diluted with dichloromethane was slowly dropped into the resulting mixture through a dropping funnel. As the reaction proceeded, precipitation of an yellow product was observed.

The reaction liquid was further stirred at room temperature for 12 hours, and then completion of the reaction was confirmed by means of thin-layer chromatography. Thereafter, the excess methyl chloroformate in the reaction liquid was hydrolyzed, and an aqueous solution of NaHCO₃ was added to the reaction liquid to separate the reaction liquid into an aqueous phase and an oily phase containing a large amount of the reaction product.

To the obtained aqueous phase was added dichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was precipitated again using acetone/dichloromethane, to obtain 0.36 g of a purified product.

The purified product obtained as above had a melting point of 180° to 181° C. when measured in accordance with a DSC method, and had m/Z=211 (100) by mass spectrum analysis.

Figure 10:
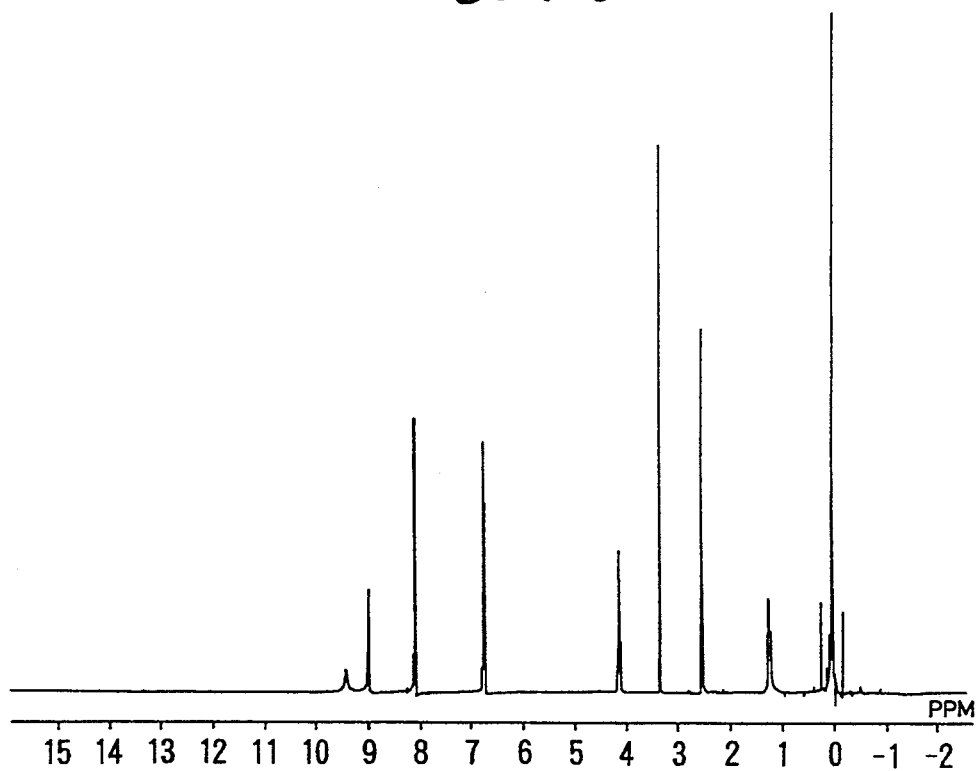
FIG. 10 is a $^1$H nucleus magnetic resonance spectrum chart of methyl-3-(p-nitrophenyl)carbazate, a novel hydrazine compound of the invention.

Further, the purified product was dissolved in DMSO (dimethyl sulfoxide). Using the resulting solution, a ¹H nucleus magnetic resonance spectrum of the purified product was measured. A chart of the obtained ¹H nucleus magnetic resonance spectrum is shown in FIG. 10.

The results obtained by analysis of peaks of this chart are as follows.

¹H nucleus magnetic resonance (δ p.p.m.)
3.61 (s, 3H, —OCH₃)
6.84 (d, 2H, 9H$_z$, ring proton)
8.08 (d, 2H, 9H$_z$, ring proton)
9.00 (s, 1H, —NH—)
9.45 (s, 1H, —NH—)

Figure 11:
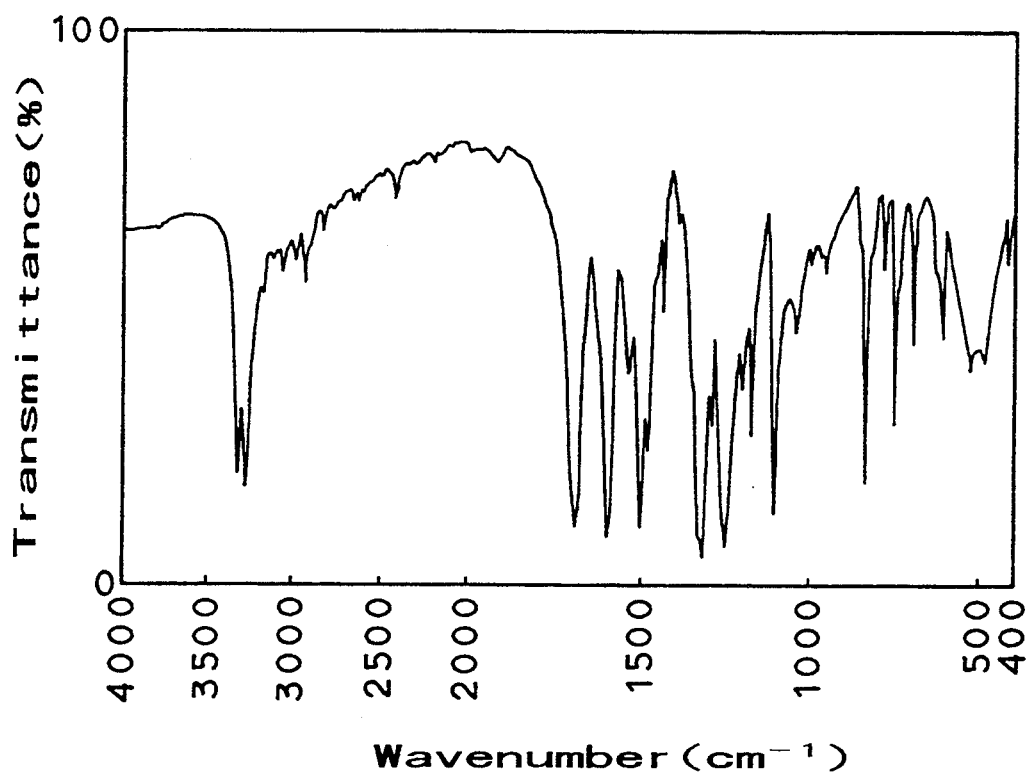
FIG. 11 is an infrared absorption spectrum chart of methyl-3-(p-nitrophenyl)carbazate, a novel hydrazine compound of the invention.

Furthermore, an infrared absorption spectrum of the purified product was measured. A chart of the obtained infrared absorption spectrum is shown in FIG. 11.

From the results obtained in the above, the purified product was identified to be methyl-3-(p-nitrophenyl) carbazate (aforementioned compound (7)).

A powder of the obtained compound (7) was measured on the SHG intensity in the same manner as described in Example 1. As a result, the SHG intensity of this powder was 19.5 times of the SHG intensity of an urea powder measured in the same manner as above.

Then, a single crystal of the aforementioned compound (7) was prepared in the same manner as described in Example 1. The obtained single crystal had a size of $30 \times 12 \times 6$ mm$^3$. Further, the single crystal of the compound (7) obtained as above was subjected to an X-ray structural analysis. As a result, the spatial group belonged to orthorhombic system (P2$_1$2$_1$2$_1$), and the lattice constants were as follows.

a = 11.48 angstroms
b = 18.51 angstroms
c = 4.70 angstroms

Furthermore, using the obtained single crystal, the intensity of the SH light was measured in the same manner as described in Example 1. As a result, the obtained intensity was a large value which was 4 times of an intensity obtained in the case of using a KTP crystal (sample length: 5 mm).

EXAMPLE 5

Into a 300 ml three-necked flask were introduced 100 ml of dichloromethane and 0.77 g of p-nitrophenylhydrazine. To the mixture in the flask was added 2.50 cc of pyridine under stirring of the mixture at room temperature, and then 1.00 cc of ethyl chloroformate having been diluted with diichloromethane was slowly dropped into the resulting mixture through a dropping funnel. As the reaction proceeded, precipitation of an yellow product was observed.

The reaction liquid was further stirred at room temperature for 12 hours, and then completion of the reaction was confirmed by means of thin-layer chromatography. Thereafter, the excess ethyl chloroformate in the reaction liquid was hydrolyzed, and an aqueous solution of NaHCO$_3$ was added to the reaction liquid to separate the reaction liquid into an aqueous phase and an oily phase containing a large amount of the reaction product.

To the obtained aqueous phase was added diichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was precipitated again using acetone/dichloromethane, to obtain 0.56 g of a purified product.

The purified product obtained as above had a melting point of 200° to 201° C. when measured in accordance with a DSC method, and had m/Z=225 (100) by mass spectrum analysis.

Figure 12:
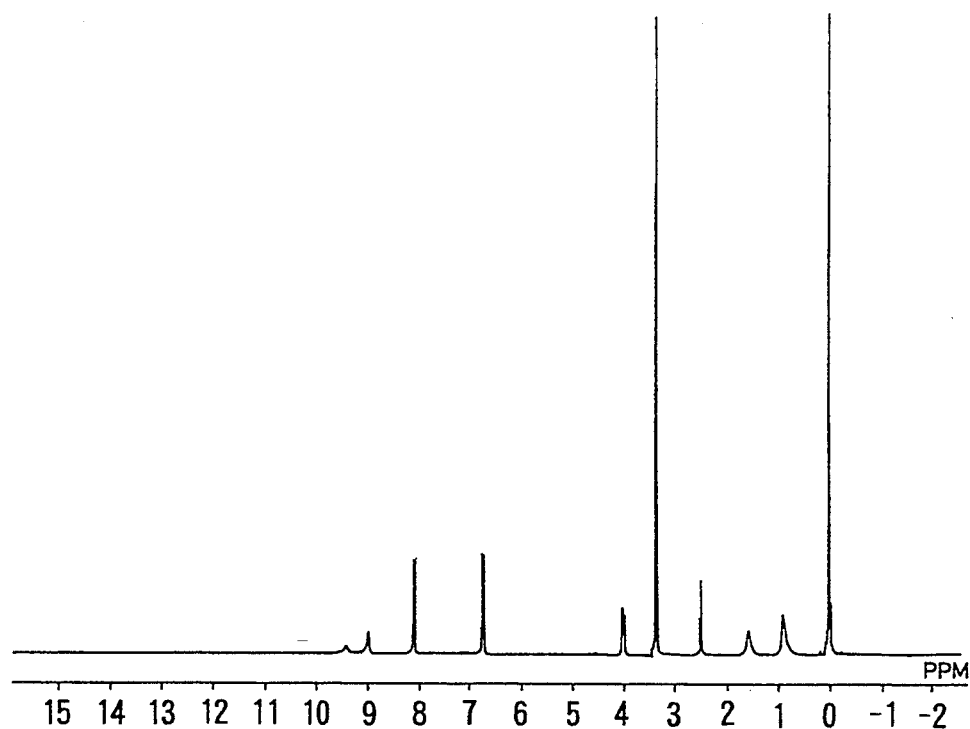
FIG. 12 is a $^1$H nucleus magnetic resonance spectrum chart of ethyl-3-(p-nitrophenyl)carbazate, a novel hydrazine compound of the invention.

Further, the purified product was dissolved in DMSO (dimethyl sulfoxide). Using the resulting solution, a $^1$H nucleus magnetic resonance spectrum of the purified product was measured. A chart of the obtained $^1$H nucleus magnetic resonance spectrum is shown in FIG. 12.

The results obtained by analysis of peaks of this chart are as follows.

$^1$H nucleus magnetic resonance ($\delta$ p.p.m.)
1.20 (s, 3H, —CH$_3$)
4.09 (s, 2H, —OCH$_2$—)
6.72 (d, 2H, 9H$_z$, ring proton)
8.08 (d, 2H, 9H$_z$, ring proton)
8.98 (s, 1H, —NH—)
9.39 (s, 1H, —NH—)

Figure 13:
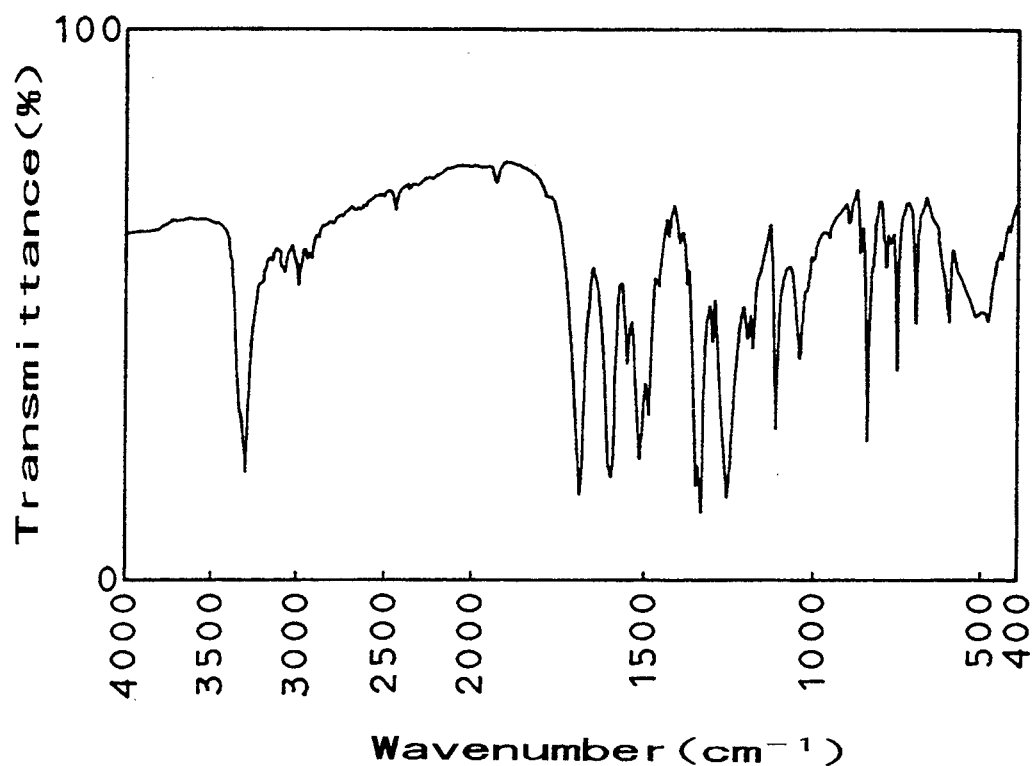
FIG. 13 is an infrared absorption spectrum chart of ethyl-3-(p-nitrophenyl) carbazate, a novel hydrazine compound of the invention.

Furthermore, an infrared absorption spectrum of the purified product was measured. A chart of the obtained infrared absorption spectrum is shown in FIG. 13.

From the results obtained in the above, the purified product was identified to be ethyl-3-(p-nitrophenyl) carbazate (aforementioned compound (8)).

A powder of the obtained compound (8) was measured on the SHG intensity in the same manner as described in Example 1. As a result, the SHG intensity of this powder was 1.0 time of the SHG intensity of an urea powder measured in the same manner as above.

Then, a single crystal of the aforementioned compound (8) was prepared in the same manner as described in Example 1. The obtained single crystal had a size of $5 \times 3 \times 1$ mm$^3$. Further, using the obtained single crystal, the intensity of the SH light was measured in the same manner as described in Example 1. As a result, the obtained intensity was a value which was 0.5 time of an intensity obtained in the case of using a KTP crystal (sample length: 5 mm).

EXAMPLE 6

Into a 200 ml twin-necked flask were introduced 50 ml of dichloromethane and 0.71 g of p-nitrophenylhydrazine. To the mixture in the flask was added 2.50 cc of pyridine under stirring of the mixture at room temperature, and then 0.8 cc of n-propyl chloroformate having been beforehand dissolved in dichloromethane was slowly dropped into the resulting mixture through a dropping funnel. As the reaction proceeded, precipitation of an yellow product was observed.

The reaction liquid was further stirred at room temperature for 12 hours, and then completion of the reaction was confirmed by means of thin-layer chromatography. Thereafter, the excess n-propyl chloroformate in the reaction liquid was hydrolyzed, and an aqueous solution of NaHCO$_3$ was added to the reaction liquid to separate the reaction liquid into an aqueous phase and an oily phase containing a large amount of the reaction product.

To the obtained aqueous phase was added dichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was precipitated again using acetone/dichloromethane, to obtain 0.35 g of a purified product.

The purified product obtained as above had a melting point of 125° to 126° C. when measured in accordance with a DSC method.

Figure 14:
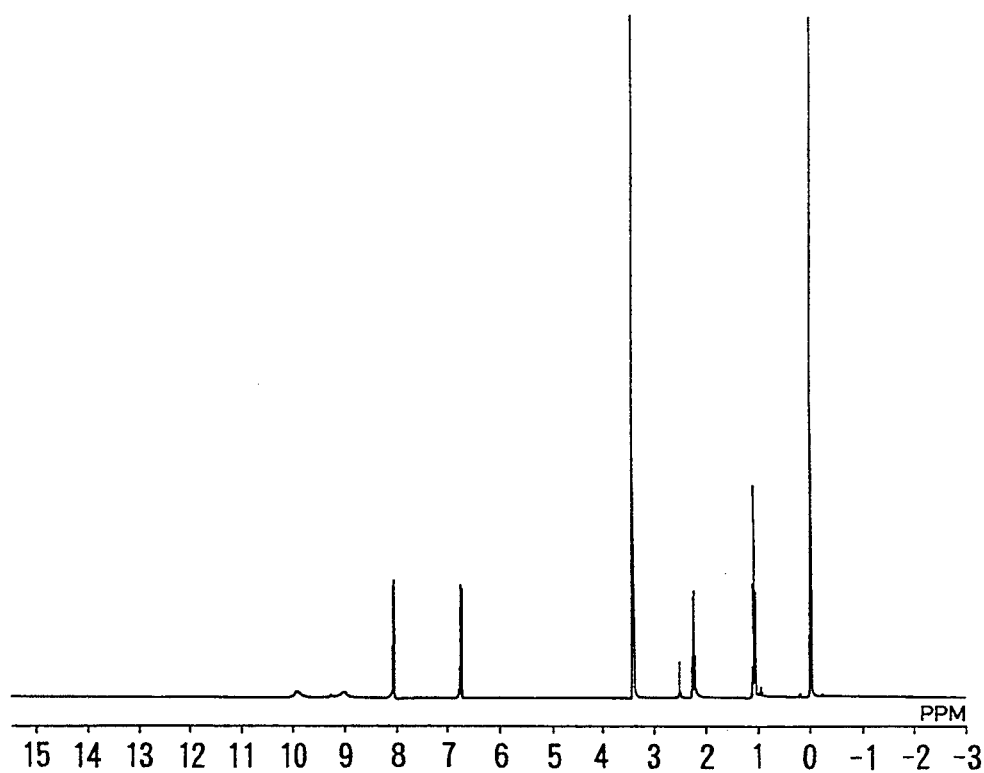
FIG. 14 is a $^1$H nucleus magnetic resonance spectrum chart of n-propyl-3-(p-nitrophenyl)carbazate, a novel hydrazine compound of the invention.

Further, the purified product was dissolved in DMSO (dimethyl sulfoxide). Using the resulting solution, a $^1$H nucleus magnetic resonance spectrum of the purified product was measured. A chart of the obtained $^1$H nucleus magnetic resonance spectrum is shown in FIG. 14.

The results obtained by analysis of peaks of this chart are as follows.

$^1$H nucleus magnetic resonance ($\delta$ p.p.m.)
0.98 (s, 3H, —CH$_3$)
1.59 (s, 2H, —CH$_2$—)
4.0 (t, 2H, 7H$_z$, —OCH$_2$—)
6.72 (d, 2H, 9H$_z$, ring proton)
8.08 (d, 2H, 9H$_z$, ring proton)
8.98 (s, 1H, —NH—)
9.39 (s, 1H, —NH—)

Figure 15:
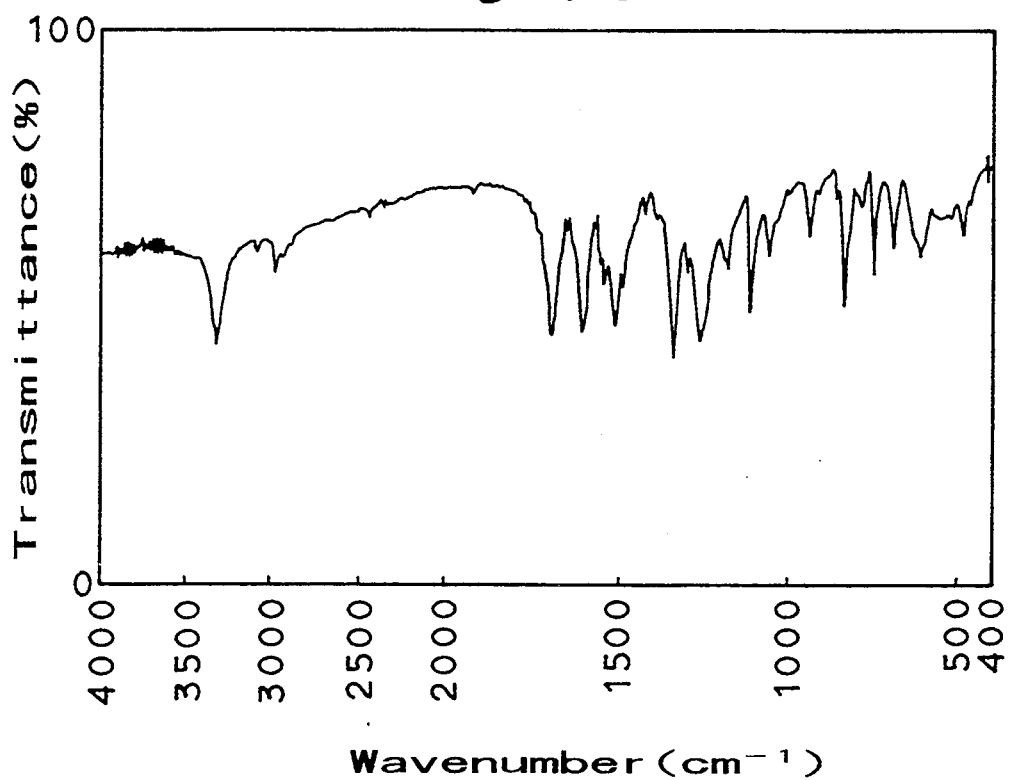
FIG. 15 is an infrared absorption spectrum chart of n-propyl-3-(p-nitrophenyl) carbazate, a novel hydrazine compound of the invention.

Furthermore, an infrared absorption spectrum of the purified product was measured. A chart of the obtained infrared absorption spectrum is shown in FIG. 15.

From the results obtained in the above, the purified product was identified to be n-propyl-3-(p-nitrophenyl)-carbazate (aforementioned compound (9)).

A powder of the obtained compound (9) was measured on the SHG intensity in the same manner as described in Example 1. As a result, the SHG intensity of this powder was 2.6 times of the SHG intensity of an urea powder measured in the same manner as above.

Then, a single crystal of the aforementioned compound (9) was prepared in the same manner as described in Example 1. The obtained single crystal had a size of 6×4×2.5 mm$^3$. Further, using the obtained single crystal, the intensity of the SH light was measured in the same manner as described in Example 1. As a result, the obtained intensity was a value which was 0.8 time of an intensity obtained in the case of using a KTP crystal (sample length: 5 mm).

EXAMPLE 7

Into a 300 ml three-necked flask were introduced 50 ml of dichloromethane and 4.62 g of p-nitrophenylhydrazine. To the mixture in the flask was added 5 cc of triethylamine under stirring of the mixture at room temperature, and then 4.5 cc of methoxyacetyl chloride was slowly dropped into the resulting mixture through a dropping funnel, to immediately give an yellow precipitate.

The reaction liquid was further stirred at room temperature for 12 hours, and then completion of the reaction was confirmed by means of thin-layer chromatography. Thereafter, the excess methoxyacetyl chloride in the reaction liquid was hydrolyzed, and an aqueous solution of NaHCO$_3$ was added to the reaction liquid to separate the reaction liquid into an aqueous phase and an oily phase containing a large amount of the reaction product.

To the obtained aqueous phase was added dichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was precipitated again using acetone, to obtain 5.735 g of a purified product (4'-nitrophenyl-methoxyacetyl carbohydrazide).

The purified product obtained as above had a melting point of 149° to 150° C. when measured in accordance with a DSC method.

Figure 16:
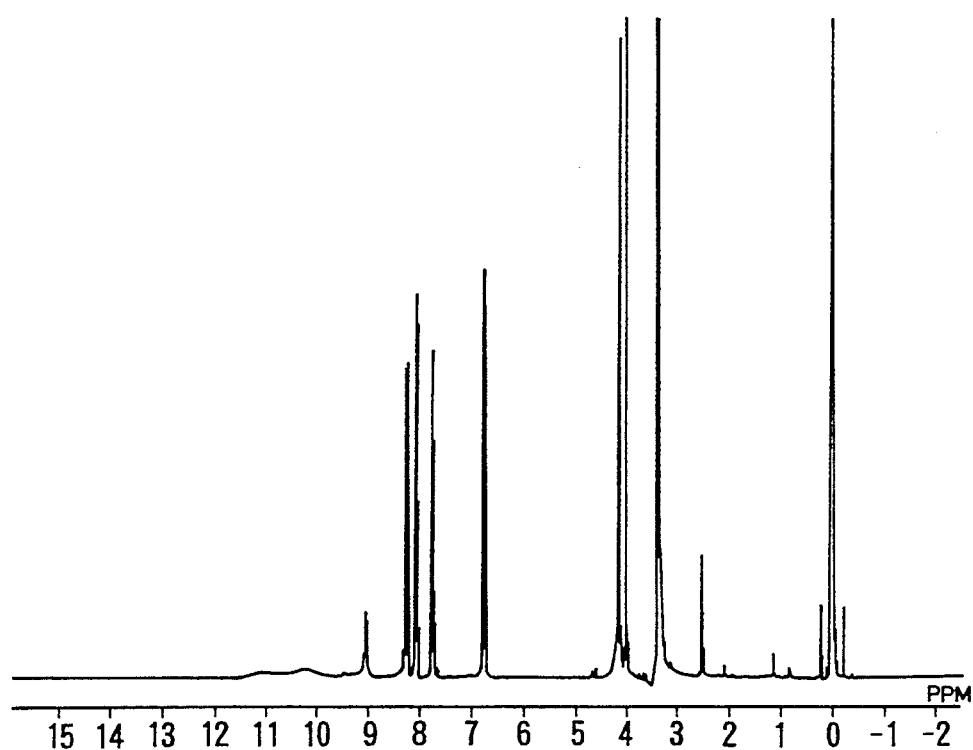
FIG. 16 is a $^1$H nucleus magnetic resonance spectrum chart of 4'-nitrophenyl-methoxyacetyl carbohydrazide, a novel hydrazine compound of the invention.

Further, the purified product was dissolved in DMSO (dimethyl sulfoxide). Using the resulting solution, a $^1$H nucleus magnetic resonance spectrum of the purified product was measured. A chart of the obtained $^1$H nucleus magnetic resonance spectrum is shown in FIG. 16.

The results obtained by analysis of peaks of this chart are as follows.

$^1$H nucleus magnetic resonance ($\delta$ p.p.m.)
4.02 (s, 2H, —CH$_2$—)
4.13 (s, 3H, —OCH$_3$—)
6.75 (d, 2H, 9H$_z$, ring proton)
8.07 (d, 2H, 9H$_z$, ring proton)
9.03 (s, 1H, —NH—)
10.14 (s, 1H, —NH—)

Figure 17:
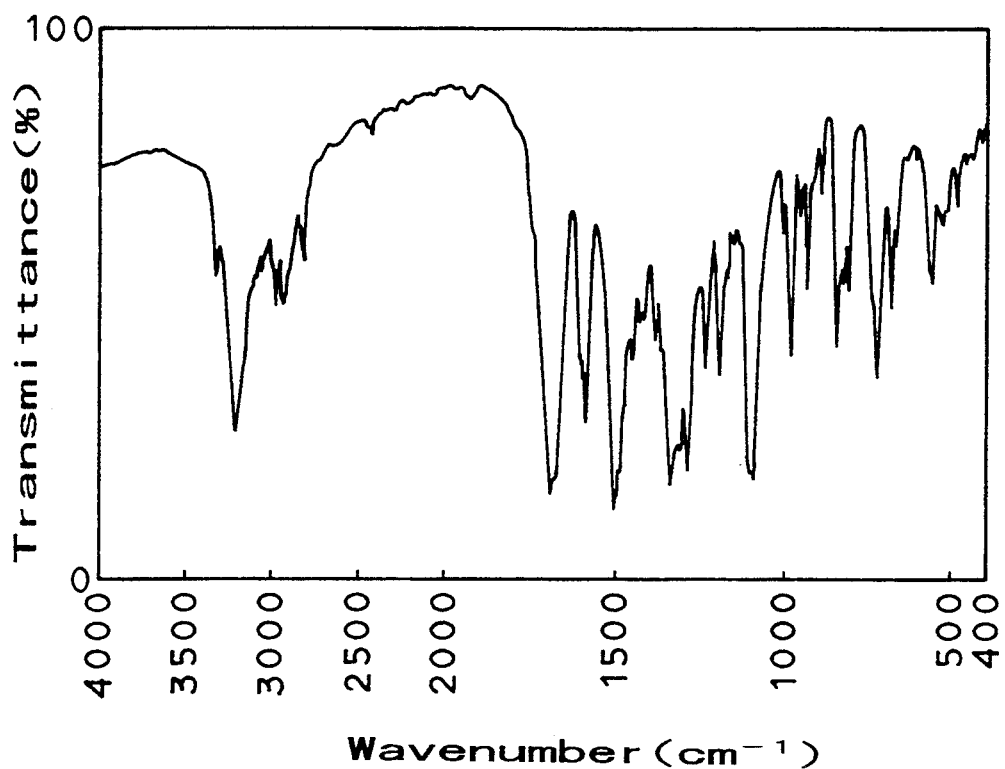
FIG. 17 is an infrared absorption spectrum chart of 4'-nitrophenyl-methoxyacetyl carbohydrazide, a novel hydrazine compound of the invention.

Furthermore, an infrared absorption spectrum of the purified product was measured. A chart of the obtained infrared absorption spectrum is shown in FIG. 17.

From the results obtained in the above, the purified product was identified to be 4'-nitrophenyl-methoxyacetyl carbohydrazide (aforementioned compound (12)).

EXAMPLE 8

Into a 300 ml three-necked flask were introduced 50 ml of dichloromethane and 1.53 g of p-nitrophenylhydrazine. To the mixture in the flask was added 3 cc of pyridine under stirring of the mixture at room temperature, and then 1.39 g of 3-methylthiopropyl chloride having been beforehand dissolved in dichloromethane was slowly dropped into the resulting mixture through a dropping funnel, to immediately give an yellow precipitate.

The reaction liquid was further stirred at room temperature for 12 hours, and then completion of the reaction was confirmed by means of thin-layer chromatography. Thereafter, the excess 3-methylthiopropyl chloride in the reaction liquid was hydrolyzed, and an aqueous solution of NaHCO$_3$ was added to the reaction liquid to separate the reaction liquid into an aqueous phase and an oily phase containing a large amount of the reaction product.

To the obtained aqueous phase was added dichloromethane to extract the reaction product remaining in the aqueous phase into the dichloromethane, and the dichloromethane containing the reaction product was withdrawn. The dichloromethane containing the reaction product was mixed with the above-obtained oily phase, and the resulting mixture solution was dried under vacuum. The obtained reaction product was precipitated again using methylene chloride/hexane mixed solvent, to obtain 1.91 g of a purified product (4'-nitrophenyl-3-methylthiopropyl carbohydrazide).

The purified product obtained as above had a melting point of 126° to 127° C. when measured in accordance with a DSC method.

Figure 18:
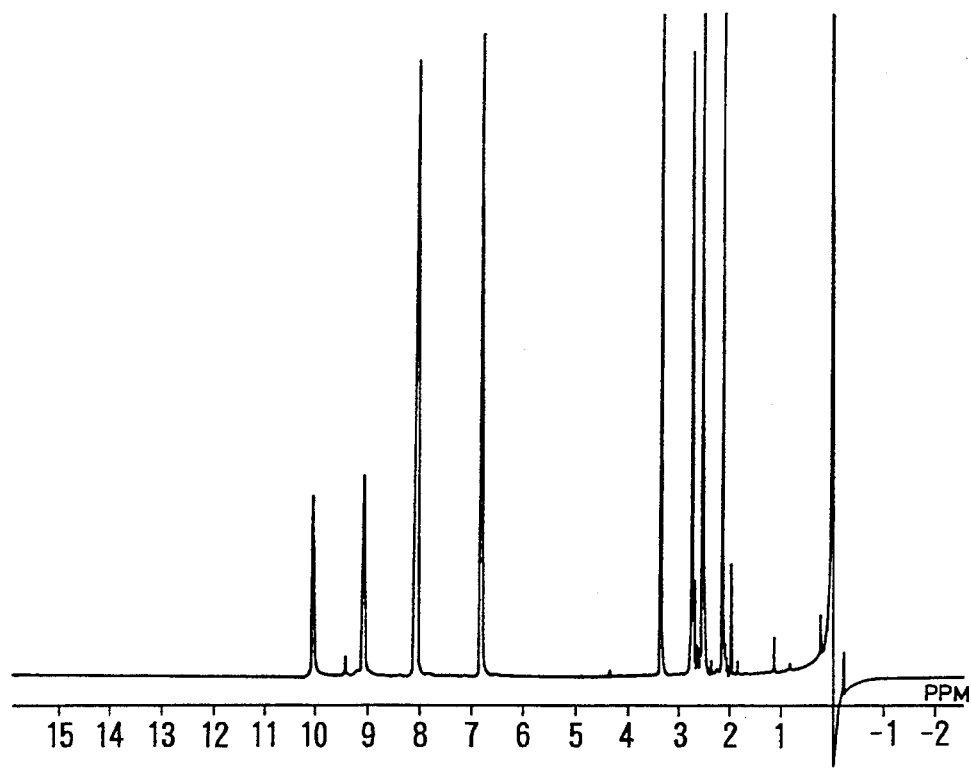
FIG. 18 is a $^1$H nucleus magnetic resonance spectrum chart of 4'-nitrophenyl-3-methylthiopropyl carbohydrazide, a novel hydrazine compound of the invention.

Furthermore, the purified product was dissolved in DMSO (dimethyl sulfoxide). Using the resulting solution, a $^1$H nucleus magnetic resonance spectrum of the purified product was measured. A chart of the obtained $^1$H nucleus magnetic resonance spectrum is shown in FIG. 18.

The results obtained by analysis of peaks of this chart are as follows.

$^1$H nucleus magnetic resonance ($\delta$ p.p.m.)
2.10 (s, 3H, —CH$_3$)
2.51 (t, 2H, 11H$_z$, —CH$_2$—)
2.73 (t, 2H, 13H$_z$, —CH$_2$—)
6.79 (d, 2H, 9H$_z$, ring proton)
8.04 (d, 2H, 9H$_z$, ring proton)
9.07 (s, 1H, —NH—)
10.03 (s, 1H, —NH—)

Figure 19:
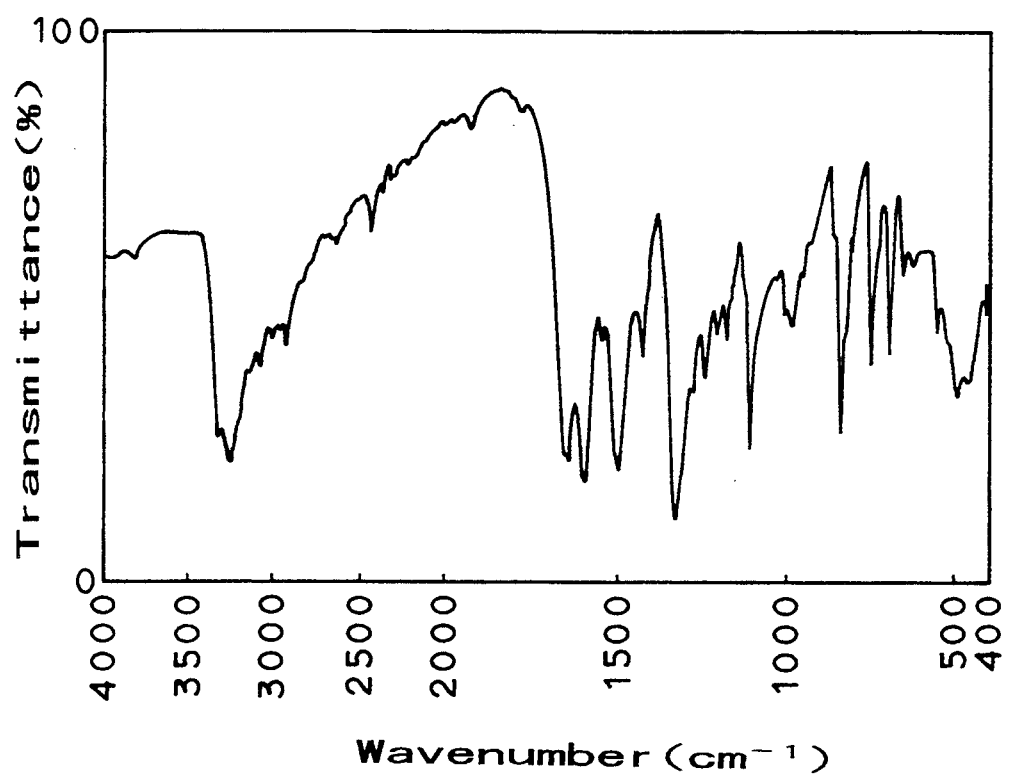
FIG. 19 is an infrared absorption spectrum chart of 4'-nitrophenyl-3-methylthiopropyl carbohydrazide, a novel hydrazine compound of the invention.

Further, an infrared absorption spectrum of the purified product was measured. A chart of the obtained infrared absorption spectrum is shown in FIG. 19.

From the results obtained in the above, the purified product was identified to be 4'-nitrophenyl-3-methylthiopropyl carbohydrazide (aforementioned compound (15)).

What is claimed is:

1. A nonlinear optical organic material composite which comprises a transparent polymer and a hydrazine compound represented by the formula (I):

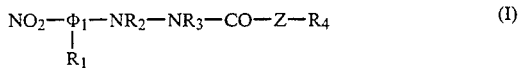

wherein $\Phi_1$ is a 5 or 6-, member heterocyclic ring; $R_1$ to $R_3$ are each independently a hydrogen atom or a group selected from the group consisting of an alkyl group, an aryl group, an aralkyl group and an alkyloxy group; $R_4$ is a hydrogen atom or a group selected from the group consisting of an alkyl group, an alkenyl group and a phenyl group; when $R_4$ is an alkyl group or an alkenyl group, the alkyl group or the alkenyl group may have an hydroxyl group and/or a halogen atom, and a divalent hetero atom or a divalent group containing a hetero atom may be present between adjacent two carbon atoms of the alkyl group or the alkenyl group; and Z is a single bond or is oxygen.

2. A nonlinear optical organic material which comprises a composite of a transparent polymer and a hydrazine compound represented by the formula:

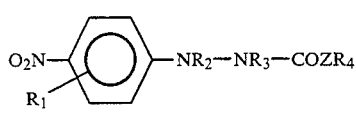

wherein $R_1$ to $R_3$ are each independently hydrogen or an alkyl group; $R_4$ is a member selected from the group consisting of an alkyl group, an alkenyl group, an alkyl group substituted by hydroxyl or halogen or both, an alkenyl group substituted by hydroxyl or halogen or both, and a divalent hetero atom or a divalent group containing a hetero atom may be present between adjacent carbon atoms of the alkyl group or the alkylene group, and a phenyl group; and Z is a direct bond or oxygen.

3. The nonlinear optical organic material composite of claim 2 which comprises a hydrazine compound wherein Z is a direct bond.

4. The nonlinear optical organic material composite of claim 2 which comprises a hydrazine compound wherein Z is oxygen.

5. The nonlinear optical organic material composite of claim 2 which comprises a hydrazine compound wherein Z is a direct bond, $R_1$ to $R_3$ are each hydrogen and $R_4$ is —CH$_2$OCH$_3$.

6. The nonlinear optical organic material composite of claim 2 which comprises a hydrazine compound wherein Z is a direct bond, $R_1$ to $R_3$ are each hydrogen and $R_4$ is —CH$_2$CH$_2$COCH$_3$.

7. The nonlinear optical organic material composite of claim 2 which comprises a hydrazine compound wherein Z is a direct bond, $R_1$ to $R_3$ are each hydrogen and $R_4$ is —CH$_2$CH$_2$—S—CH$_3$.

8. The nonlinear optical organic material composite of claim 2 which comprises a hydrazine compound wherein Z is a direct bond, $R_1$ to $R_3$ are each hydrogen and $R_4$ is —CH$_2$CH$_2$—CH=CHCH$_3$.

9. The nonlinear optical organic material composite of claim 2 which comprises a hydrazine compound wherein Z is a direct bond, $R_1$ to $R_3$ are each hydrogen and $R_4$ is —CH$_2$OH.

10. The nonlinear optical organic material composite of claim 2 which comprises a hydrazine compound wherein Z is a direct bond, $R_1$ to $R_3$ are each hydrogen and $R_4$ is —CH(OH)CH$_3$.

11. A nonlinear optical organic material composite which comprises a transparent polymer and a hydrazine compound represented by the formula:

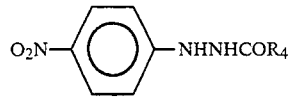

wherein $R_4$ is $C_1$ to $C_4$ alkyl or phenyl.

12. The nonlinear optical organic material composite of claim 11 which comprises a hydrazine compound wherein $R_4$ is $C_2$ to $C_3$ alkyl.

13. The nonlinear optical organic material composite of claim 11 which comprises a hydrazine compound wherein $R_4$ is phenyl.

14. A nonlinear optical organic material composite which comprises a transparent polymer and a hydrazine compound represented by the formula:

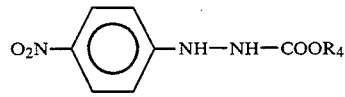

wherein $R_4$ is $C_1$ to $C_4$ alkyl or phenyl.

15. The nonlinear optical organic material composite of claim 14 which comprises a hydrazine compound wherein $R_4$ is methyl.

16. The nonlinear optical organic material composite of claim 14 which comprises a hydrazine compound wherein $R_4$ is ethyl.

17. The nonlinear optical organic material composite of claim 14 which comprises a hydrazine compound in which $R_4$ is phenyl.

18. A nonlinear optical element which comprises a transparent polymer and a single ,crystal of a hydrazine compound represented by the formula:

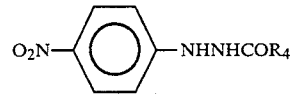

wherein $R_4$ is $C_1$ to $C_4$ alkyl or phenyl, and
wherein said single crystal is rectangular parallelepiped having no less than 1 mm$^3$.

19. The nonlinear optical element of claim 18 which comprises a hydrazine compound wherein $R_4$ is $C_2$ to $C_3$ alkyl.

20. The nonlinear optical element of claim 18 which comprises a hydrazine compound wherein $R_4$ is phenyl.

21. A nonlinear optical element which comprises a transparent polymer and a single crystal of a hydrazine compound represented by the formula:

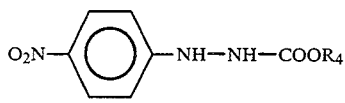

wherein $R_4$ is $C_1$ to $C_4$ alkyl or phenyl, and
wherein said single crystal is rectangular parallelepiped having not less than 1 mm$^3$.

22. The nonlinear optical element of claim 21 which comprises a hydrazine compound wherein $R_4$ is methyl.

23. The nonlinear optical element of claim 21 which comprises a hydrazine compound wherein $R_4$ is ethyl.

24. The nonlinear optical of claim 21 which comprises a hydrazine compound in which $R_4$ is phenyl.

25. A method for converting laser light into a different wave length which comprises directing laser light at a nonlinear optical element comprising a single crystal of a hydrazine compound represented by the formula:

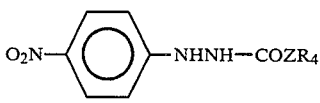

wherein $R_4$ is a member selected from the group consisting of $C_1$ to $C_4$ alkyl and phenyl; and Z is a direct bond or oxygen.

26. The method of claim 25 wherein in the hydrazine compound Z is a direct bond.

27. The method of claim 25 wherein in the hydrazine compound Z is oxygen.

28. The method of claim 27 wherein in the hydrazine compound $R_4$ is $C_2$ to $C_3$ alkyl.

29. The method of claim 26 wherein in the hydrazine compound $R_4$ is phenyl.

30. The method of claim 27 wherein in the hydrazine compound $R_4$ is methyl.

31. The method of claim 27 wherein in the hydrazine compound $R_4$ is ethyl.

32. The method of claim 27 wherein in the hydrazine compound $R_4$ is phenyl.

33. A nonlinear optical element which comprises a transparent polymer and a single crystal of a hydrazine compound represented by the formula (I):

$$NO_2-\Phi_1-NR_2-NR_3-CO-Z-R_4 \qquad (I)$$
$$\hspace{1.2cm}|$$
$$\hspace{1.2cm}R_1$$

wherein $\Phi_1$ is a 5 or 6-member heterocyclic ring; $R_1$ to $R_3$ are each independently a hydrogen atom or a group selected from the group consisting of an alkyl group, an aryl group, an aralkyl group and an alkyloxy group; $R_4$ is a hydrogen atom or a group selected from the group consisting of an alkyl group, an alkenyl group and a phenyl group; when $R_4$ is an alkyl group or an alkenyl group, the alkyl group or the alkenyl group may have an hydroxyl group and/or a halogen atom, and a divalent hetero atom or a divalent group containing a hetero atom may be present between adjacent two carbon atoms of the alkyl group or the alkenyl group; and Z is a single bond or is oxygen.

34. A nonlinear optical element which comprises a transparent polymer and a single crystal of a hydrazine compound represented by the formula

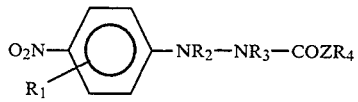

wherein $R_1$ to $R_3$ are each independently hydrogen or an alkyl group; $R_4$ is a member selected from the group consisting of an alkyl group, an alkenyl group, an alkyl group substituted by hydroxyl or halogen or both, an alkenyl group substituted by hydroxyl or halogen or both, and a divalent hetero atom or a divalent group containing a hetero atom may be present between adjacent carbon atoms of the alkyl group or the alkylene group, and a phenyl group; and Z is a direct bond or oxygen.

35. A method for converting laser light into a different wave length which comprises directing laser light at a nonlinear optical element comprising a single crystal of a hydrazine compound represented by formula (I):

$$NO_2-\Phi_1-NR_2-NR_3-CO-Z-R_4 \qquad (I)$$
$$\hspace{1.2cm}|$$
$$\hspace{1.2cm}R_1$$

wherein $\Phi_1$ is a 5 or 6-member heterocyclic ring; $R_1$ to $R_3$ are each independently a hydrogen atom or a group selected from the group consisting of an alkyl group, an aryl group, an aralkyl group and an alkyloxy group; $R_4$ is a hydrogen atom or a group selected from the group consisting of an alkyl group, an alkenyl group and a phenyl group; when $R_4$ is an alkyl group or an alkenyl group, the alkyl group or the alkenyl group may have an hydroxyl group and/or a halogen atom, and a divalent hetero atom or a divalent group containing a hetero atom may be present between adjacent two carbon atoms of the alkyl group or the alkenyl group; and Z is a single bond or is oxygen.

36. A method for converting laser light into a different wave length which comprises directing laser light at a nonlinear optical element comprising a single crystal of a hydrazine compound represented by the formula:

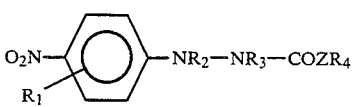

wherein $R_1$ to $R_3$ are each independently hydrogen or an alkyl group; $R_4$ is a member selected from the group consisting of an alkyl group, an alkenyl group, an alkyl group substituted by hydroxyl or halogen or both, an alkenyl group substituted by hydroxyl or halogen or both, and a divalent hetero atom or a divalent group containing a hetero atom may be present between adjacent carbon atoms of the alkyl group or the alkylene group, and a phenyl group; and Z is a direct bond or oxygen.

* * * * *